US008785177B2

(12) United States Patent
Yu et al.

(10) Patent No.: US 8,785,177 B2
(45) Date of Patent: Jul. 22, 2014

(54) METHODS FOR NANO-MECHANOPORATION

(71) Applicants: Min-Feng Yu, Norcross, GA (US);
Kyungsuk Yum, Berkeley, CA (US);
Ning Wang, Champaign, IL (US)

(72) Inventors: Min-Feng Yu, Norcross, GA (US);
Kyungsuk Yum, Berkeley, CA (US);
Ning Wang, Champaign, IL (US)

(73) Assignee: The Board of Trustees of the University of Illinois, a body Corporate and Politic of the State of Illinois, Urbana, IL (US)

( * ) Notice: Subject to any disclaimer, the term of this patent is extended or adjusted under 35 U.S.C. 154(b) by 0 days.

(21) Appl. No.: 13/669,233

(22) Filed: Nov. 5, 2012

(65) Prior Publication Data
US 2013/0137129 A1   May 30, 2013

Related U.S. Application Data

(60) Provisional application No. 61/555,710, filed on Nov. 4, 2011.

(51) Int. Cl.
*C12N 5/00*   (2006.01)
(52) U.S. Cl.
USPC ......... 435/285.2; 977/904; 977/906; 977/916
(58) Field of Classification Search
None
See application file for complete search history.

(56) References Cited

U.S. PATENT DOCUMENTS

| | | | |
|---|---|---|---|
| 5,786,219 | A | 7/1998 | Zhang et al. |
| 6,063,629 | A | 5/2000 | Knoblauch |
| 6,251,658 | B1 | 6/2001 | Henderson et al. |
| 6,645,757 | B1 | 11/2003 | Okandan et al. |
| 6,846,668 | B1 | 1/2005 | Garman et al. |
| 2003/0059936 | A1 | 3/2003 | Baumann et al. |
| 2003/0068821 | A1 | 4/2003 | Lois-Caballe et al. |
| 2003/0228695 | A1 | 12/2003 | Nakamura et al. |
| 2005/0137525 | A1 | 6/2005 | Wang et al. |
| 2006/0149280 | A1 | 7/2006 | Harvie et al. |
| 2007/0087436 | A1 | 4/2007 | Miyawaki et al. |
| 2008/0027384 | A1 | 1/2008 | Wang et al. |
| 2008/0213899 | A1 | 9/2008 | Olgac |
| 2009/0148880 | A1 | 6/2009 | Fuhr et al. |
| 2009/0295408 | A1 | 12/2009 | Aizenberg et al. |
| 2012/0091235 | A1 | 4/2012 | Li et al. |

FOREIGN PATENT DOCUMENTS

| | | |
|---|---|---|
| JP | 58-076091 | 5/1983 |
| WO | WO 2008/046051 | 4/2008 |

OTHER PUBLICATIONS

Hara et al. "A practical device for pinpoint delivery of molecules inot multiple neurons in culture." (2006) Brain Cell Biology, vol. 35: 229-237.*
Almquist et al. (Mar. 30, 2010) "Fusion of biomimetic stealth probes into lipid bilayer cores," Proc. Natl. Acad. Sci. U. S. A. 107:5815-5820.
Bogle et al. (Summer 2010) "Nanofountain Probes for Single-Cell Transfection: A Comparative Study Assessing Invasiveness," Nanoscape. 7(1):33-37.
Chakravarty et al. (published online Jul. 18, 2010) "Delivery of molecules into cells using carbon nanoparticles activated by femtosecond laser pulses," Nat. Nanotechnol. 5:607-611.
Chen (2007) "A cell nanoinjector based on carbon nanotubes," Proc. Natl. Acad. Sci. U. S. A. 104:8218-8222.
Chopra et al. (1998) "Measurement of the Elastic Modulus of a Multi-Wall Boron Nitride Nanotube," Solid State Comm. 105(5):297-300.
Cumings et al. (2004) "Field Emission and Current-Voltage Properties of Boron Nitride Nanotubes," Solid State Comm.129:661-664.
Demczyk et al. (2002) "Direct Mechanical Measurement of the Tensile Strength and Elastic Modulus of Multiwalled Carbon Nanotubes," Mater. Sci. and Engr. 1334:173-178.
Derfus et al. (2004) "Intracellular delivery of quantum dots for live cell labeling and organelle tracking," Adv. Mater. 16, 961-966.
Haas et al. (2001) "Single-cell electroporation for gene transfer in vivo," Neuron. 29:583-591.
Han et al. (2005) "A molecular delivery system by using AFM and nanoneedle," Biosens. Bioelectron. 20:2120-2125.
Hara et al. (2006) "A practical device for pinpoint delivery of molecules into multiple neurons in culture," Brain Cell Biol. 35:229-237.
Japan Report (Apr. 17, 1987) "Japan Report: Science and Technology," Foreign Broadcast Information Service. Document No. JPRS-JST-87-011. Arlington, Virginia. pp. 1-8.
Judkewitz et al. (published online May 14, 2009) "Targeted single-cell electroporation of mammalian neurons in vivo," Nat. Protocols. 4:862-869.
Kihara et al. (published online Jun. 6, 2009) "Development of a method to evaluate caspase-3 activity in a single cell using a nanoneedle and a fluorescent probe," Biosens. Bioelectron. 25:22-27.
Kitamura et al. (2008) "Targeted patch-clamp recordings and single-cell electroporation of unlabeled neurons in vivo," Nat. Methods. 5:61-67.

(Continued)

*Primary Examiner* — Jon P Weber
*Assistant Examiner* — Teresa E Knight
(74) *Attorney, Agent, or Firm* — Lathrop & Gage LLP

(57) ABSTRACT

Methods for creating a transient nanoscale opening in a cell membrane and methods for transporting a desired species through the nanoscale opening are provided. A nano-sized needle-like tip can be used to mechanically slice the cell membrane to create a transient, localized nanoscale slit. The nanoscale slit may be used for transferring exogenous molecules into a living cell.

28 Claims, 10 Drawing Sheets

(56) References Cited

OTHER PUBLICATIONS

Knoblauch et al. (1999) "A galinstan expansion femtosyringe for microinjection of eukaryotic organelles and prokaryotes," Nat. Biotechnol. 17:906-909.
Loh et al. (Jul. 2009) "Nanofountain-Probe-Based High-Resolution Patterning and Single-Cell Injection of Functionalized Nanodiamonds," Small. 5(4):1667-1674.
Luby-Phelps (2000) "Cytoarchitecture and physical properties of cytoplasm: Volume, viscosity, diffusion, intracellular surface area," Int. Rev. Cytol. 192:189-221.
Luo et al. (2000) "Synthetic DNA delivery systems," Nat. Biotechnol. 18:33-37.
Matsuda et al. (May 1, 2008) "A Novel Method for In Situ Hybridization in Fungal Cells Based on Pricking Micro-Injection of Photobiotin Labeled Probes," Journal of Phytopathology. 141(2):133-142.
McNeil (2003) "Direct introduction of molecules into cells," *Curr. Protoc. Cell. Biol.* 20.1.1-20.1.7.
McNeil et al. (1984) "A method for incorporating macromolecules into adherent cells," J. Cell Biol. 89:1556-1564.
McNeil et al. (1987) "Glass Beads Load Macromolecules into Living Cells," J. Cell Science. 88:669-678.
McNeil et al. (2003) "Plasma membrane disruption: Repair, prevention, adaptation," Annu. Rev. Cell Dev. Biol. 19:697-731.
McNeil et al. (2005) "An emergency response team for membrane repair," Nat. Rev. Mol. Cell Biol. 6:499-505.
Mehier-Humbert et al. (2005) "Physical methods for gene transfer: Improving the kinetics of gene delivery into cells," Adv. Drug Delivery Rev. 57:733-753.
Meister et al. (Jun. 10, 2009) "FluidFM: combining atomic force microscopy and nanofluidics in a universal liquid delivery system for single cell applications and beyond," Nano Lett. 9:2501-2507.
Mellgren (published online Sep. 1, 2010) "A Plasma Membrane Wound Proteome Reversible Externalization of Intracellular Proteins Following Reparable Mechanical Damage," J. Biol. Chem. 285:36597-36607.
Poncharal et al. (Mar. 5, 1999) "Electrostatic Deflection and Electromechanical Resonances of Carbon Nanotubes," Science. 283:1513-1516.
Qian et al. (Nov. 2002) "Mechanics of Carbon Nanotubes," Appl. Mech. Res. 55(6):495-533.
Reddy et al. (Jul. 27, 2001) "Plasma Membrane Repair is Mediated by Ca2+-Regulated Exocytosis of Lysosomes," Cell. 106:157-169.
Riveline et al. (published online Jun. 7, 2009) "'Injecting' yeast," Nat. Methods. 6:513-514.
Ruan et al. (2007) "Imaging and tracking of tat peptide-conjugated quantum dots in living cells: New insights into nanoparticle uptake, intracellular transport, and vesicle shedding," J. Am. Chem. Soc. 129:14759-14766.
Salvetat et al. (1999) "Mechanical Properties of Carbon Nanotubes," Appl. Phys. A 69:255-260.
Sato et al. (1993) "Gene Introduction Into Mouse Blastocysts via 'Pricking'" Mol. Reprod. Dev. 34:349-356.
Singhal et al. (published online Dec. 12, 2010) "Multifunctional carbon-nanotube cellular endoscopes," Nat. Nanotechnol. 6:57-64.
Steinhardt et al. (1994) "Cell membrane resealing by a vesicular mechanism similar to neurotransmitter release," Science. 263:390-393.
Stephens et al. (2001) "The many ways to cross the plasma membrane," Proc. Natl. Acad. Sci. U. S. A. 98:4295-4298.
Tirlapur et al. (2002) "Targeted transfection by femtosecond laser," Nature. 418:290-291.
Wong et al. (Jun. 2010) "Dynamic Actuation Using Nano-Bio Interfaces," Materials Today. 13(6):14-22.
Wu at al. (published online May 6, 2009) "A Miniature Probe for Ultrasonic Penetration of a Single Cell," Sensors. 9:3325-3336.
Yamamoto et al. (1982) "The 'pricking' method: A new efficient technique for mechanically introducing foreign DNA into the nuclei of culture cells," Exp. Cell Res. 142:79-84.
Yamamoto et al. (2004) "Intracellular Introduction of a Fixed Quantity of Substances by Pricking Cells Using a Modified Microscope," Exp. Cell Res. 135(2):341-345.
Yum et al. (published online Apr. 14, 2009) "Mechanochemical delivery and dynamic tracking of fluorescent quantum dots in the cytoplasm and nucleus of living cells," Nano Lett. 9:2193-2198.
Yum et al. (published online Dec. 9, 2009) "Nanoneedle: A multifunctional tool for biological studies in living cells," Nanoscale. 2:363-372.
Yum at al. (published online May 24, 2010) "Biofunctionalized nanoneedles for the direct and site-selective delivery of probes into living cells," Biochim. Biophys. Acta, Gen. Subj. 1810:330-338.
Yum et al. (published online Sep. 8, 2010) "Electrochemically controlled deconjugation and delivery of single quantum dots into the nucleus of living cells," Small. 6:2109-2113.

\* cited by examiner

US 8,785,177 B2

METHODS FOR NANO-MECHANOPORATION

STATEMENT REGARDING FEDERALLY SPONSORED RESEARCH OR DEVELOPMENT

This invention was made with government support under grant GM072744 awarded by National Institutes of Health and grant CBET-0933223 awarded by the National Science Foundation. The government has certain rights in the invention.

CROSS-REFERENCE TO RELATED APPLICATIONS

This application claims the benefit of U.S. Provisional Application No. 61/555,710, filed Nov. 4, 2011, which is hereby incorporated by reference in its entirety.

BACKGROUND

Intracellular delivery of biologically significant species is a vital technique to study intracellular processes and biophysical properties of living cells (Stephens, D. J. & Pepperkok, R. Proc. Natl. Acad. Sci. U.S.A. 98, 4295-4298 (2001)). Previous intracellular delivery methods include carrier-mediated methods, such as viral vectors and cationic lipids and polymers, and physical methods, such as microinjection, electroporation, and laser irradiation.

The carrier-mediated methods are effective in delivering molecules into an entire cell population, but they often associate with undesired side effects (e.g., viral toxicity, mutagenicity, and host-immune responses), endocytic degradation and trapping, and cell-type dependent efficiency, partly because of their use of active transfer mechanisms of cells (Luo, D. & Saltzman, W. M. Nat. Biotechnol. 18, 33-37 (2000), Ruan, G., Agrawal, A., Marcus, A. I. & Nie, J. Am. Chem. Soc. 129, 14759-14766 (2007)).

Several physical techniques have been proposed which involve mechanical disruption of the membrane. For example, a cell may be loaded through a microinjection technique in which the cell membrane is penetrated with a needle and macromolecules are injected into the cytoplasm through the needle. Cells may also be loaded through wounding of cells with glass beads (McNeil and Warder, 1987, J. Cell Science, 88, 669-678, through scraping adherent cells from a substrate ("scrape loading", McNeil et al., 1984, J. Cell Biol., 89, 1556-1564), or by "pricking" cells with a needle (Yamamoto et al., 1982, Exp. Cell Res. 142, 79). Physical methods such as microinjection and laser irradiation can circumvent the cell-type dependency, but generally aim to deliver molecules into targeted individual cells. More recently, nanotechnology-based tools, such as atomic force microscopy and nanoneedles, have also been used to intracellular delivery. These new delivery methods use nanoscale tools (e.g., nanotube-based nanoneedles) that can be operated with nanoscale resolutions and thus allow high precision delivery, enabling new experimental strategies that require to manipulate living cells with high spatial and temporal resolutions and with minimal invasiveness. For example, nanoneedle-based delivery of quantum dots into the cytoplasm and nucleus of living cells has been demonstrates, made possible due to the high-aspect ratio nanoneedles with nanoscale diameters (<~100 nm) (4-6) (Derfus, A. M., Chan, W. C. W. & Bhatia, S. N., Adv. Mater. 16, 961-966 (2004), Knoblauch, M., et al. Nat. Biotechnol. 17, 906-909 (1999), Tirlapur, U. K. & Konig, Nature 418, 290-291 (2002)).

SUMMARY

In one aspect, the invention provides a method for creating a transient nanoscale opening in the membrane of a cell, the method employing a tool with a nanoscale tip, such as a needle-like tip which is nanoscale in its diameter or characteristic width and elongated along a longitudinal axis. Because the formation of the opening or pore in the cell membrane is mechanically induced, the process is termed "mechanoporation." In an embodiment, the method involves lateral movement of the tool after its insertion in the membrane to "slice" the membrane and create an opening of controlled size and duration. The opening can be used to introduce a variety of agents, for example exogenous molecules or particles, into the cell. Such techniques can be useful for transfection as well as fluorescence imaging.

In one aspect of the methods of the invention, a probe having a tip is inserted into the cell so that the tip of the probe is located within the intracellular environment. The small diameter of the tip can allow entry of the tip into the interior of the cell with minimal damage to the cell membrane. In an embodiment, the tip is less than or equal to 300 nm, from 10 nm to 300 nm, from 50 nm to 200 nm, or from 50 nm to 100 nm in diameter. In an embodiment, the probe includes a nanoscale portion having a diameter or characteristic width is less than or equal to 300 nm. In different embodiments, the length of the nanoscale portion of the probe is 10-1000 times, 25-500 times, or 50 to 500 time the diameter or characteristic width of the nanoscale portion of the probe. In another aspect, the invention provides probes suitable for use with the methods of the invention.

The probe may be inserted by contacting the exterior of the cell membrane with the end of the tip, then advancing the tip in a longitudinal direction until penetrating the membrane. Preferably, insertion of the tip into the membrane creates an initial entrance opening in the membrane, but not an opening permeable to species inside or outside the cell. In an embodiment, the initial entrance opening in the membrane is approximately the same size as the size of the tip in the region of contact with the membrane. In an embodiment, the cell lacks a cell wall. In different embodiments, the cell may be ex vivo or in vitro.

The inserted tip is then moved in at least one direction transverse to the longitudinal axis of the tip, thereby creating an opening in the membrane. In an embodiment, the small diameter of the tip and the controlled tip speed together permit a relatively narrow "slit-like" opening to be formed. In an embodiment, the width of the slit-like opening in the membrane is not much greater than that of the tip diameter. In an embodiment, the opening is "nanoscale" and has at least one dimension (e.g. its width) less than 1 micrometer. In an embodiment, the lateral motion of the tip does not cause disruption of the cell membrane surrounding the opening. In different embodiments, the speed of tip motion during either longitudinal or lateral translation is greater than zero and less than 100 microns/sec, greater than zero and less than 50 microns/sec, greater than zero and less than 25 microns/sec, greater than zero and less than 10 microns/sec, greater than 5 and less than 100 microns/sec, greater than 5 and less than 50 microns/sec, greater than 5 and less than 25 microns/sec, from 0.25 microns/sec to 5 microns/sec or from 0.5 microns/sec to 2 microns/sec. The process of forming the opening may be viewed as "slicing" or "unzipping" the membrane. In an embodiment, this opening is permeable to a desired species or agent (30), so that the opening is a permeable opening. This aspect of the process is schematically illustrated in FIG. 1. In an embodiment, the tip of the probe (25) is cycled back and forth between two travel endpoints, forming a slit-like opening. The outlined arrow indicates the back and forth motion of the probe (shown as a needle-like probe in FIG. 1) The size of the permeable opening (20) created can depend on several factors: the diameter of the tip at its contact region with the membrane (10), the amplitude of the cyclic motion and the frequency of cyclic motion. In another embodiment, the tip of the probe may be moved in a plurality of directions transverse to the longitudinal axis of the tip, which can create an opening having a shape other than a simple slit. For example, the tip may be moved or cycled in a first transverse direction and then moved or cycled in a second transverse direction. In an embodiment, the angle between two of the transverse directions may be other than 180 degrees.

In order to form a transient opening, the membrane has at least one mechanism to re-seal the nanoscale opening created in the process. In an embodiment, the frequency of the tip's cyclic or lateral movement can be selected in comparison to the time constant related to the membrane repair mechanism. In different embodiments, the total duration of the tip's cyclic movement is from 1 second to 5 minutes, from 5 seconds to 50 seconds, from 1 minute to 5 minutes, or from 30 seconds to 3 minutes. In an embodiment, the recovery time for a given location in the membrane to reseal is given by $\tau$, In an embodiment, the period of cyclic motion of the probe is less than $\tau$.

Typically, the cell is immersed in an extracellular solution. When an opening is created in the membrane which is larger than the diameter of the probe, appropriately sized molecules or particles from the cell medium (extracellular solution) can diffuse into the cell. The quantity of molecules or particles diffusing into the cell depends in part on the concentration of the solution, the size of the opening, and the duration of the opening. In an embodiment, the width of the opening or slit is approximately the diameter of the tip and the length of the opening or slit can be from 1 nm to several micrometers depending on the amplitude of the oscillation. In an embodiment, the length of the opening or slit is less than one micrometer. The opening is sustained during the cyclic movement period of the tip. In an embodiment, the quantity of molecules or particles delivered to the cell may be controlled to one attoliter. After the cyclic movement period and retraction of the tip from the cell, the membrane is believed to reseal quickly. Membrane resealing can be due to several processes including an intrinsic thermodynamically-favored self-sealing process and $Ca^{2+}$-triggered exocytosis (McNeil, P. L. & Steinhardt, R. A., *Annu. Rev. Cell Dev. Biol.* 19, 697-731 (2003); McNeil, P. L. & Kirchhausen, T., *Nat. Rev. Mol. Cell Biol.* 6, 499-505 (2005); Steinhardt, R. A., et al., *Science* 263, 390-393 (1994); Reddy, A., et al., *Cell* 106, 157-169 (2001)).

In an embodiment, the invention provides a method for creating a transient nanoscale opening in the membrane of a cell, the method comprising the steps of:
  a. providing a probe and a cell, the probe having a longitudinal axis and a solid tip end, the diameter of the tip being from 10 to 300 nm and the cell being immersed in an extracellular solution;
  b. contacting the end of the tip with the outer surface of the cell membrane;
  c. following step b), piercing through the membrane of the cell by moving the probe in a longitudinal direction until the free end of the tip is located within the intracellular environment of the cell;
  d. following step c), creating an opening in the membrane of the cell by inducing motion of the tip in at least two directions transverse to the longitudinal axis of the probe, the motion of the tip comprising
    i) motion of the tip in a first direction transverse to the longitudinal axis of the probe for a first lateral displacement distance; and
    ii) motion of the tip in a second direction transverse to the longitudinal axis of the probe for a second lateral displacement distance, the second direction being other than the first direction;
  e. following step d), retracting the tip completely from the cell and allowing the cell membrane to reseal the created opening, wherein the cell is substantially stationary during steps b) through e) and the longitudinal speed of the probe in step c) and the lateral speed of the probe in step d) are greater than zero and less than 10 microns/sec.

In an embodiment, the invention provides a method for creating a transient opening in the membrane of a cell, the method comprising the steps of:
  a. providing a probe and a cell, the probe having a longitudinal axis and a needle tip end, the diameter of the needle tip being from 50 to 300 nm and the cell being immersed in an extracellular solution;
  b. contacting the end of the needle tip with the outer surface of the cell membrane;
  c. following step b), piercing through the membrane of the cell by moving the needle tip in a substantially longitudinal direction until the end of the needle tip is located within the intracellular environment of the cell;
  d. following step c), creating an opening in the membrane of the cell by laterally oscillating the tip of the probe;
  e. following step d), retracting the needle tip from the cell and allowing the cell membrane to reseal the nanoscale opening with its own biophysical repair mechanism, wherein the cell is substantially stationary during steps b) through e) and the speed of the probe in steps c) and d) is greater than zero and less than 100 microns/sec.

Alternately, the opening may be created by moving the tip of the probe in at least two different directions transverse to the longitudinal axis of the probe. In an embodiment, the angle between two of the transverse directions may be other than 180 degrees.

In an embodiment, the size of the desired opening created in the cell membrane is determined based on the size of the agent or species to be transported through the membrane, so that the opening is permeable to the desired species. The opening may therefore be termed a "permeable opening." The agent or species to be transported through the membrane may be exogenous (initially present outside the membrane) or endogenous. In an embodiment, the size of the opening permits transport of molecules from 1000 Dalton up to more than 1000 kilo-Dalton. In another embodiment, the size of the opening permits transport of molecules or nanoparticles having an effective or actual diameter from 2 nm to 250 nm.

In an embodiment, the invention provides a method for transporting a desired species through a transient nanoscale opening in the membrane of a cell, the method comprising the steps of:
  a. providing a probe and a cell, the probe having a longitudinal axis and a tip end, the diameter of the tip being from 50 to 300 nm the cell being immersed in an extracellular solution and the desired species being provided either in the extracellular solution or within the cell;
  b. contacting the end of the tip with the outer surface of the cell membrane;
  c. following step b), piercing through the membrane of the cell by moving the probe in a longitudinal direction until the end of the tip is located within the intracellular environment of the cell;

d. following step c), creating a permeable opening in the membrane of the cell by inducing motion of the tip in at least two directions transverse to the longitudinal axis of the probe, the motion of the tip comprising
   i) motion of the tip in a first direction transverse to the longitudinal axis of the probe for a first lateral displacement distance; and
   ii) motion of the tip in a second direction transverse to the longitudinal axis of the probe for a second lateral displacement distance, the second direction being other than the first direction;
e. transporting the desired species through the permeable opening;
f. following step e), retracting the tip from the cell and allowing the cell membrane to reseal the created opening;
   wherein the cell is substantially stationary during steps b) through f) and both the longitudinal speed of the probe in step c) and the lateral speed of the probe in step d) are greater than zero and less than 10 microns/sec.

In another aspect, the invention provides a method for transporting a desired species through a transient opening in the membrane of a cell, the method comprising the steps of:
a. providing a probe and a cell, the probe having a longitudinal axis and a needle tip end, the diameter of the needle tip being from 50 to 300 nm, the cell being immersed in an extracellular solution and the desired species being provided either in the extracellular solution or within the cell;
b. contacting the end of the needle tip with the outer surface of the cell membrane;
c. following step b), piercing through the membrane of the cell by moving the needle tip in a substantially longitudinal direction until the end of the needle tip is located within the intracellular environment of the cell;
d. following step c), creating a permeable opening in the membrane of the cell by laterally oscillating the tip of the probe;
e. following step d), transporting the desired species through the permeable opening;
f. following step e), retracting the needle tip from the cell and allowing the cell membrane to reseal the nanoscale opening with its own biophysical repair mechanism.
   wherein the cell is substantially stationary during steps b) through f) and the speed of the probe in steps c) and d) is greater than zero and less than 100 microns/sec.

Alternately, the opening may be created by moving the tip of the probe in at least two different directions transverse to the longitudinal axis of the probe. In an embodiment, the angle between two of the transverse directions may be other than 180 degrees.

In different embodiments, the agent or species introduced into the cell may be a chemical species or a biomolecular species. In different embodiments, the agent species may be immobilized small molecules (e.g. drugs, chemical compounds), biopolymers, biologics (e.g. peptides, polypeptides, proteins, DNA, RNA, antibodies), protein assemblies (e.g. viruses), vectors, plasmids, or nanoparticles. "Biological molecule" is used broadly to refer to an agent that has an at least partially biologically-based composition (e.g., nucleotides, peptides, polynucleotides, polypeptides, genes, gene fragments, or compositions that are made by biological cells). Any one or more of these agent species may be packaged to facilitate delivery to regions of interest in the cell, including by normal cellular processes. In an embodiment, the agent may be functionalized to bind a structure of interest within the cell. For example, the agent may be functionalized with an antibody.

In an embodiment, the agent introduced into the cell comprises a detectable tag. For example, the agent may be an antibody that is itself labeled, such as with a fluorescence marker or radiolabel, a quantum dot, or a nanoparticle. In an embodiment, the agent may comprise particles which are fluorescent, magnetic, radioactive, electrically conducting, or absorptive/colored. In an embodiment, the particles are nanoparticles. As used herein, nanoparticles have an average size greater than or equal to 1 nm and less than 1000 nm. In an embodiment, the average size of the nanoparticles is 10-20 nm. When the agents comprise a detectable tag, the methods of the invention may include detecting the detectable tag to monitor the distribution of the agent in an intracellular environment.

In an embodiment, the agent may comprise fluorescent particles. Fluorescent particles known to the art include fluorescently labeled microspheres and nanospheres. These particles include surface labeled spheres, spheres labeled throughout, and spheres possessing at least one internal fluorescent spherical zone (as described in U.S. Pat. No. 5,786,219 to Zhang et al.) Other fluorescent particles known to the art include quantum dots (QDots or QDs). These include naturally fluorescent nanoparticles that have optical properties that are tunable with their size. Commercially available quantum dots include nanometer-scale particles comprising a core, shell, and coating. The core may be made up of a few hundred to a few thousand atoms of a semiconductor material (often cadmium mixed with selenium or tellurium). A semiconductor shell (which may be zinc sulfide) surrounds and stabilizes the core. An amphiphilic polymer coating may encase this core and shell, providing a water-soluble surface that can be differentially modified. Commercially available quantum dots include QDots®, available from Invitrogen, which have reported peak emission wavelengths at 565 nm, 605 nm, 625 nm, 655 nm, 705 nm, and 800 nm. The quantum dots may be functionalized. For example, the QDs may be functionalized with a biotin binding protein such as streptavidin, a biomolecule such as an antibody, a target molecule complex or combinations thereof.

In an aspect the methods of the invention may be used to introduce a therapeutic into the cell. Therapeutic is used broadly to refer to a composition that provides a benefit to the cell. In an aspect the therapeutic is a chemical compound or a drug useful in treating a disease state. In an aspect, the therapeutic is a biological entity such as a protein, polypeptide, antibody, polynucleotide such as DNA or RNA. In an aspect, the biological entity is packaged to facilitate delivery and/or incorporation into the biological cell. For example, the DNA may be packaged into a vector to facilitate controlled incorporation into the cellular genome. In an aspect, the agent is used for genetic engineering, wherein the cellular DNA is modified by introducing a piece of DNA that is not found in the native DNA, to express DNA that is not normally expressed, or to silence expression of DNA that is normally expressed.

In another aspect, the methods of the invention may be used to introduce a diagnostic into the cell. The diagnostic may be used to identify or detect genetic mutations, diseased cells (e.g., cancerous cells or cells infected by a virus and/or bacteria), identify proteins such as proteins that are associated with bacterial or viral infection, or to identify any physical abnormality or defect in a cell.

The nano-mechanoporation approach of the invention can have several advantages for intracellular delivery. First, the slender nano-sized portion of the probe can gently penetrate through the thin cell membrane without inducing severe mechanical deformation and physical damage to the cell membrane and the near membrane cytoskeletal structures. Second, using a needle-like nano-sized portion of the probe to slice through the cell membrane can minimize the drag force and thus the perturbation to the cell. Third, the gap width of the slit in the membrane may be defined by the diameter of the nano-sized portion of the probe and be of nanoscale dimension, which facilitates energy efficient self-sealing of the opening (effective for small disruptions of <0.2 μm) (McNeil, P. L. & Steinhardt, R. A., *Annu. Rev. Cell Dev. Biol.* 19, 697-731 (2003); McNeil, P. L. & Kirchhausen, T., *Nat. Rev. Mol. Cell Biol.* 6, 499-505 (2005)). Fourth, the length of the slit is expected to be dependent on the amplitude and frequency of the slicing motion and the self-sealing rate of the membrane, and is thus externally controllable from essentially zero up to several 100 nanometers or more, which provides the possibility of a delivery method with semi-quantitative control over the amount of delivery in the extreme small quantity range. Fifth, the methods of the invention can minimally involve additional processes beyond mechanical means; the involvement of other processes, such as electrical or electrochemical processes may be detrimental to cells that are sensitive to electrical signal and ionic stimulations, such as muscle cells and neurons

DETAILED DESCRIPTION

Figure 1:
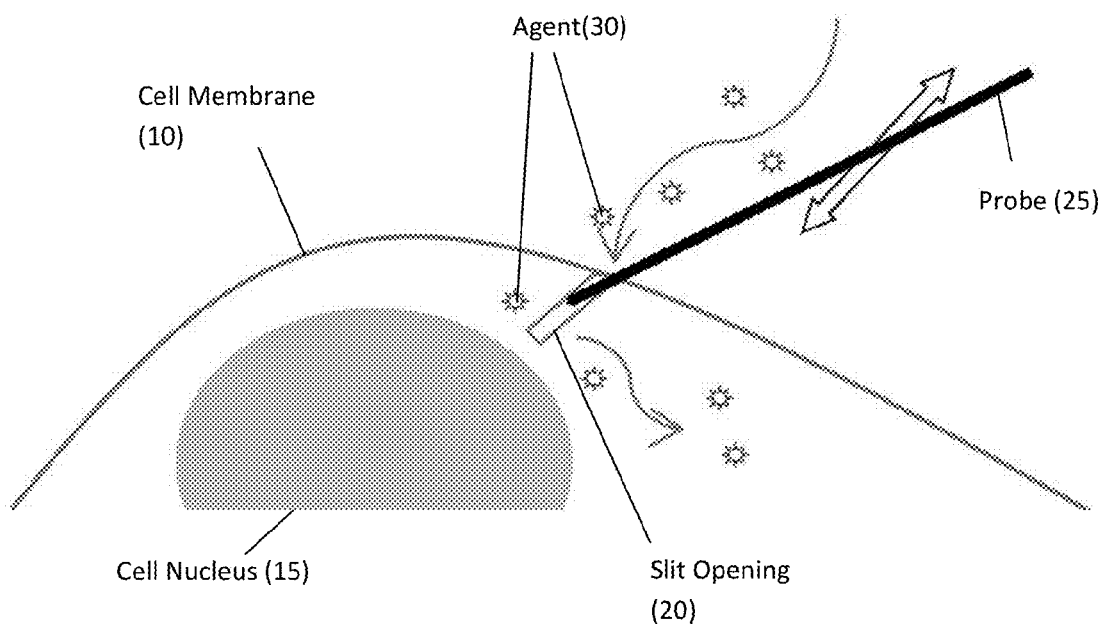
FIG. 1. Schematic of the nano-mechanoporation delivery method.
Figure 2:
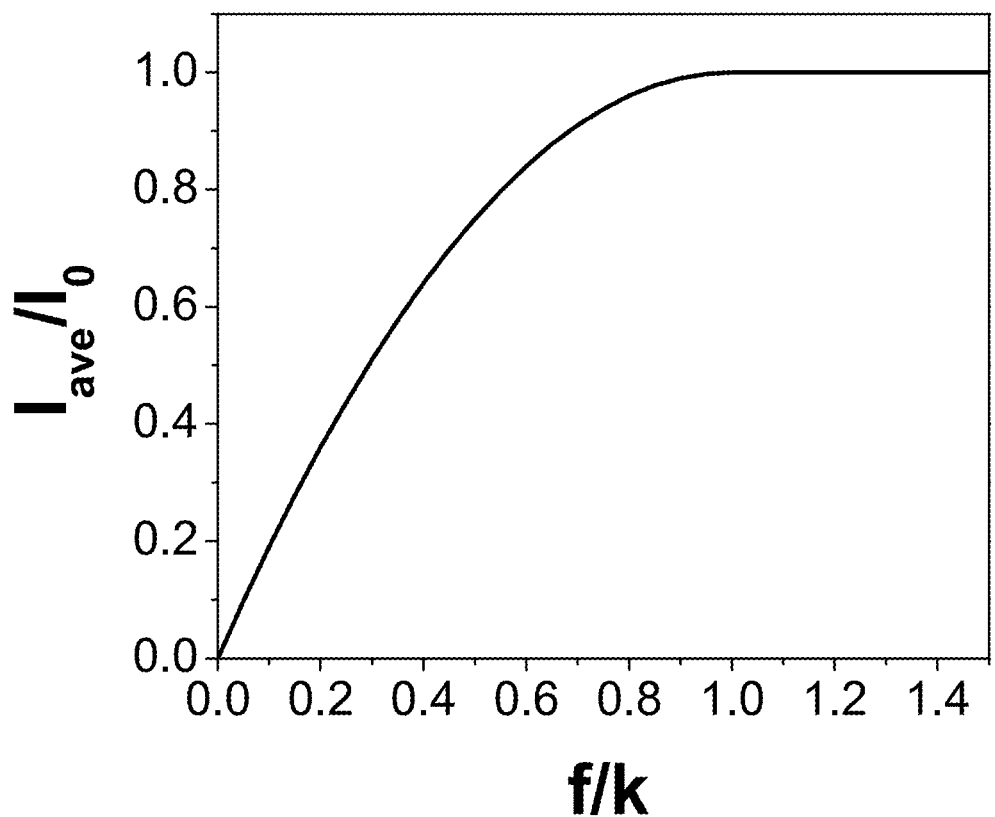
FIG. 2. The ratio of the average length of the nanoscale slit $l_{ave}$ to the actual displacement of the nanoneedle $l_0$ as a function of the ratio of the frequency of the lateral motion of the nanoneedle, f, to the molecular recombination constant, k.

In an embodiment, cells suitable for use with the methods of the invention do not have a cell wall. In different embodiments, the cell may be an animal cell or a protist cell. The cell may be an adherent cell or a nonadherent cell. In an embodiment, the techniques of the invention may be useful for small cells of only a couple of micrometers in size or cells with limited adhesion. In an embodiment, the cell is substantially stationary during its interaction with the probe, so that the relative motion of the probe and the cell is primarily determined by the motion of the probe. In different embodiments, the absolute value of the ratio of the lateral distance moved by the cell to the translation distance of the probe is greater than or equal to zero and less than 1, less than 0.5, less than 0.25 or less than 0.1.

In different embodiments, the biological cell is in vitro or ex vivo. The biological cell may comprise an isolated cell and may remain viable during and after the membrane piercing process. The intracellular environment may be the nucleus, other organelle, or the cytoplasm. The intracellular environment may also be sub-nuclear.

In one aspect, the invention provides probes suitable for use with the methods of the invention. Typically, the probe includes a nanoscale portion having a diameter or characteristic width which is nanoscale; the length of the nanoscale portion of the probe need not be nanoscale. The nanoscale portion of the probe may be referred to as a nanoprobe. In an embodiment, the diameter or characteristic width of the nanoscale portion of the probe may be less than or equal to 300 nm. In an embodiment, the nanoscale portion of the probe is elongated along a longitudinal axis and "needle-like" in shape and can be referred to as a "needle nanoprobe", "needle tip" or "nanoneedle." As used herein, a "needle-like" shape has a relatively high aspect ratio (for example, length at least 10 times the diameter) and may or may not be tapered at its tip end (e.g. tapered to a point like a sewing needle). In different embodiments, the length of the nanoprobe may be at least 10 times the diameter, at least 25 times the diameter or at least 50 times the diameter. In an embodiment, the length of the nanoprobe may be greater than 1 or 2 micrometers. In an embodiment, the nanoprobe cross-section perpendicular to the longitudinal axis is generally circular. The outer diameter of the nanoscale portion of the probe may be constant or varying along the length of the nanoprobe. For example, the nanoprobe may be generally cylindrical in shape. A first portion of the nanoprobe may also be generally cylindrical, with a second portion in the vicinity of the junction with the support being of larger diameter. The tip portion of such a nanoprobe may be of smaller diameter. The nanoprobe may also be smoothly or stepwise tapered. The diameter of a portion of the nanoprobe may be from 50 to 300 nm, from 50 nm to 100 nm, or from 100 nm to 300 nm. In an embodiment, the very end of the nanoprobe has a diameter between 10 nm and 300 nm. The nanoprobe may be solid, rather than having a hollow interior or may have a hollow interior which is sealed from contact with the intracellular environment. The probe may also be a hollow micropipette having a tapered end with the length of the tapered end having a diameter less than several hundred nanometers, a length longer than several microns and a side opening near the tapered end.

Furthermore, the nanoprobe may be shaped to minimize or avoid permanent change or damage to a biological cell or tissue, or a constituent thereof. In this manner, the tip may be sharpened to a shape analogous to a needle to facilitate entry through the membrane, passage through the cytoplasm, and/or entry into an organelle without undue disruption. Elongation to a high aspect ratio of the needle nanoprobe, where the diameter of the tip portion that enters the cell is small, such as less than or equal to 300 nm, less than or equal to 100 nm, or from 1 nm and 10 nm (at the tip end that makes initial contact and entry with the extracellular membrane) and 100 nm to 500 nm (toward the other end that connects the nanoprobe to the probe "handle") can further reduce unwanted disruption without compromising the integrity and fidelity of the nanoprobe. The radius of curvature at the tip of the nanoprobe may be from 20 to 100 nm or from 20 to 50 nm.

The nanoprobe may comprise a nanotube or a nanotube coated with a thin film. Suitable films include metals such as gold and platinum or polymers. The thickness of the film may be from 5 to 20 nm. If the nanotube has a hollow interior, application of a film to the nanotube may seal the end of the nanotube. The nanotube may be a boron nitride nanotube coated with a film, such as a gold film. The length of such a nanoprobe may be from 10 microns to 30 microns. Nanotube materials can exhibit extraordinary mechanical, electrical and/or chemical properties, which has stimulated substantial interest in developing applied technologies exploiting these properties. For example, nanotubes can have very high Young's modulus values. Multi-walled carbon nanotubes have been measured to have Young's modulus values between 0.1 and 1.33 TPa, with the Young's modulus being dependent upon the degree of order within the tube walls (Demczyk et al., 2002, Mater. Sci. and Engr. 1334, 173-178; Salvetat et al., 1999, Appl. Phys. A 69, 255-260). Multi-walled boron nitride nanotubes have been measured to have a Young's modulus of about 1.22 TPa (Chopra et al., 1998, Solid State Comm, 105(5), 297-300).

As used herein, the term "nanotube" refers to a tube-shaped discrete fibril typically characterized by a substantially constant diameter of typically about 1 nm to about 100 nm, preferably about 2 nm to about 50 nm. In addition, the nanotube typically exhibits a length greater than about 10 times the diameter, preferably greater than about 100 times the diameter. The term "multi-wall" as used to describe nanotubes refers to nanotubes having a layered nested-cylinder structure. The layers are disposed substantially concentrically about the longitudinal axis of the fibril. A variety of multi-walled nanotube compositions are known to the art, including, but not limited to, carbon, boron nitride, carbon nitride, carbon boron nitride, and sulfides. In an embodiment, such a "nanotube" is used in this application purely from the consideration of its excellent mechanical property and its hollow nature is not exploited.

Boron nitride nanotubes comprise boron combined with nitrogen. In an embodiment, the nanotubes comprise essentially only boron and nitrogen. Boron nitride nanotubes may contain low levels of impurities or can be doped with other elements or molecules. Typically the concentration of dopants is less than 1%. Besides doping, nitrogen vacancies are also possible in boron nitride. Boron nitride nanotubes are inherently large band-gap semiconductors and thus almost insulators. Boron nitride nanotubes can be made by a variety of methods including arc discharge, laser heating, and oven heating. Boron nitride nanotubes have been reported to be a good dielectric material up to about 10V (Cumings, J. and Zettl, A., 2004, Solid State Communications. 129, 661-664).

The probe will typically further comprise a support portion connected to the nanoprobe, at least a portion of the support portion having a larger diameter than the largest diameter of the nanoprobe. The support portion may be at least generally tapered in shape, with the nanoprobe being located at the smaller diameter end of the support. For example, the nanoprobe may be located at the tip or apex of a support. The support may be a sharpened tungsten tip. The nanoprobe may be connected to the support portion by a polymer-based adhesive material, by a coating film, by direct bonding between the materials of the nanoprobe and the support portion, or combinations thereof.

For example, a nanoprobe such as a boron nitride nanotube with or without a surface coating may be attached to a larger diameter "handle", such as a sharpened tungsten tip or a pulled glass tip. The attachment may be made with glue such as a small droplet of curable epoxy to provide mechanical connection.

The nanoprobe may be inserted into the cell membrane by contacting the tip of the nanoprobe with the exterior of the membrane, then advancing the tip of the nanoprobe in a longitudinal direction until the tip penetrates the membrane. The membrane may deform prior to membrane penetration. In an embodiment, the tip of the nanoprobe is advanced slowly to help limit damage to the membrane. Use of relatively slow longitudinal probe speeds can also limit lateral vibration of nanoprobe during longitudinal translation. In an embodiment, motion of the probe tip during this stage of the process is substantially longitudinal, so that the lateral distance traveled by the probe tip during this stage of the process is much less than the longitudinal distance traveled by the probe tip. In an embodiment, the lateral travel distance during the penetration step is less than 5% of the longitudinal travel distance.

Insertion of the nanoprobe tip into the membrane creates an initial entrance opening in the membrane. In an embodiment, the initial entrance opening in the membrane is approximately the same size as the portion of the probe located within the membrane The inserted probe may then be moved or oscillated in at least one direction transverse to the longitudinal axis of the probe, thereby creating a permeable opening in the membrane. A probe with a nanoscale portion of high aspect ratio may experience some lateral bending during movement of the probe. In an embodiment, the longitudinal travel distance is theoretically zero but practically will have a nonzero value due to the lateral bending of the nanoscale portion of the probe. In an embodiment, motion of the probe tip is substantially transverse to the longitudinal axis of the probe so that the longitudinal distance traveled by the probe tip during this stage of the process is much less than the lateral distance traveled by the probe tip In an embodiment, the longitudinal travel distance during the oscillation step is less than 5% of the lateral travel distance. In an embodiment, the nanoprobe is oscillated back and forth between two positions passing the initial entrance position and the lateral travel distance is the lateral distance between the first and the second position. In different embodiment, the number of cycles is from 5 to 50, from 5 to 25, or from 5 to 10.

Typically, the tip of the nanoprobe is moved or oscillated by moving the support portion of the probe laterally to the longitudinal axis of the probe. In an embodiment, the nanoprobe and/or the handle element are designed to have sufficient stiffness for satisfactory transmission of the oscillation to the tip of the nanoprobe and minimization of undesired lateral vibration of the probe during longitudinal translation of the tip of the nanoprobe. The tip of the nanoprobe may be moved or oscillated by connecting the probe to a positioning component and then moving or oscillating the positioning component to impart the desired motion to the probe. The lateral distance traversed by the tip of the probe may be less than that traversed by the positioning component due to the bending of the slender nanoprobe experiencing drag when slicing through the cell membrane. In different embodiments, the lateral distance traveled by the positioning component may be from 100 nm to 5 micrometers, from 0.5 micrometers to 5 micrometers, from 1.0 micrometers to 5 micrometers, or from 0.5 micrometers to 3 micrometers. In different embodiments, the average speed of the positioning component during either longitudinal or lateral translation is greater than zero and less than 100 microns/sec, greater than zero and less than 50 microns/sec, greater than zero and less than 25 microns/sec, greater than zero and less than 10 microns/sec, from 0.25 microns/sec to 5 microns/sec or from 0.5 microns/sec to 2 microns/sec. The position of probe may be controlled by a micromanipulator or motion-control stage In an embodiment, the probe is attached to one or more stages which allow precise control of motion along x, y, and z directions. Coarse motion in x, y, and z directions may be provided by one type of stage and fine motion by another type of stage, as is known to those skilled in the art. Suitable stages for this purpose are also known to those skilled in the art and include, but are not limited to, combinations of Burleigh inchworm stages and piezodriven flexure stages. An imaging device, for example an optical microscope, may be used to assist in positioning of the probe.

In an aspect, insertion of the nanoprobe into a biological cell or organelle thereof, does not permanently adversely affect the cell. In particular, interruption to the integrity of a membrane or other biological envelope is transient or sufficiently minor that the cell remains viable and does not suffer a significant increase in the likelihood or rate of cell death compared to a cell that has not undergone probe insertion. As used herein, "viable" refers to a cell that does not experience a significant increase in cell death, such as by apoptosis or necrosis. In particular, a cell undergoing a process disclosed herein is said to remain viable if there is not a significant change in cell death compared to an equivalent cell that has not undergone the process Accordingly, the term "needle" as used herein reflects the aspect of the invention where the insertable portion of the probe minimally effects biological tissue or cell, and is unlikely to permanently damage or other adversely affect the tissue or cell to which the probe is introduced.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or method or elements of a device, is understood to encompass those compositions, methods and devices consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. Any preceding definitions are provided to clarify their specific use in the context of the invention.

EXAMPLE

A solid nanoneedle-based intracellular delivery method is described, named nano-mechanoporation, which uses a nanoneedle to mechanically slice the cell membrane to create a transient, localized nanoscale slit for transferring exogenous molecules into a living cell. The delivery of fluorescent dextrans, phalloidin, and quantum dot nanoparticles through the localized nanoscale slit into living HeLa cells is demonstrated. A physical model of the nano-mechanoporation process shows that the amount of the target molecules delivered into cells can be controlled by changing the duration, the frequency, and the displacement of the nanoneedle movement during the delivery process. The simple procedure of the nano-mechanoporation can be adapted to the standard biological techniques and other nanotechnology-based methods, introducing new strategies for studying intracellular processes and biophysical properties of living cells, and especially small cells.

Intracellular delivery is a basic technique for studying intracellular processes and biophysical properties of living cells (Stephens, D. J. & Pepperkok, R. Proc. Natl. Acad. Sci. U.S.A. 98, 4295-4298 (2001)). Previous intracellular delivery methods include carrier-mediated methods, such as viral vectors and cationic lipids and polymers mediated ones Luo, D. & Saltzman, W. M. Nat. Biotechnol. 18, 33-37 (2000); Ruan, G et al. J. Am. Chem. Soc. 129, 14759-14766 (2007); Derfus, A. M. et al., Adv. Mater. 16, 961-966 (2004)), and physical methods, such as microinjection, electroporation, and laser irradiation (Derfus, A. M. et al., Adv. Mater. 16, 961-966 (2004); Knoblauch, M., et al., Nat. Biotechnol. 17, 906-909 (1999); Tirlapur, U. K. & Konig, K., Nature 418, 290-291 (2002); Riveline, D. & Nurse, P., Nat. Methods 6, 513-514 (2009); Chakravarty, P., et al., Nat. Nanotechnol. 5, 607-611 (2010)). The carrier-mediated methods are effective in delivering molecules into an entire cell population, but they are often associated with undesired side effects (e.g., viral toxicity and host-immune responses), endocytic degradation and trapping, and cell-type dependent efficiency, partly because of their use of active transfer mechanisms of cells (Ruan, G et al. J. Am. Chem. Soc. 129, 14759-14766 (2007); Chakravarty, P., et al., Nat. Nanotechnol. 5, 607-611 (2010); Mehier-Humbert, S. & Guy, R. H. Adv. Drug Delivery Rev. 57, 733-753 (2005)). The physical methods, such as microinjection and laser irradiation (Knoblauch, M., et al., Nat. Biotechnol. 17, 906-909 (1999); Tirlapur, U. K. & Konig, K., Nature 418, 290-291 (2002); Chakravarty, P., et al., Nat. Nanotechnol. 5, 607-611 (2010)), circumvent the cell-type dependency, but generally aim to deliver molecules into individual cells. Additionally, the microinjection, widely used in the biological sciences, often induces cell membrane damage, especially in plant and small animal cells, associated with insertion of a relatively large conical micropipette (~1 μm in diameter) (Knoblauch, M., et al., Nat. Biotechnol. 17, 906-909 (1999)). More recently, nanotechnology-based methods, such as single-cell electroporation with a pulled micropipette (Haas, K., et al. Neuron 29, 583-591 (2001); Kitamura, K., et al., Nat. Methods 5, 61-67 (2008); Judkewitz, B., et all, Nat. Protocols 4, 862-869 (2009)), atomic force microscope tip (Han, S. W., et al. Biosens. Bioelectron. 20, 2120-2125 (2005); Hara, C. et al. Brain Cell Biol. 35, 229-237 (2006); Kihara, T. et al. Biosens. Bioelectron. 25, 22-27 (2009)) and nanoneedle, (Chen, X., et al. Proc. Natl. Acad. Sci. U.S.A. 104, 8218-8222 (2007); Yum, K., et al. Nano Lett. 9, 2193-2198 (2009); Yum, K., et al. Small 6, 2109-2113 (2010); Singhal, R. et al. Nat. Nanotechnol. 6, 57-64 (2011)) have also been used for intracellular delivery for single-cell level studies. These new methods use nanoscale tools (e.g., nanotube-based nanoneedles) that can be operated with nanoscale resolution, and thus allow delivery with high spatial and temporal resolutions to targeted single cells, enabling new experimental strategies that require high-precision delivery and manipulation of single living cells with minimal invasiveness. (Kitamura, K., et al., Nat. Methods 5, 61-67 (2008); Judkewitz, B., et all, Nat. Protocols 4, 862-869 (2009); Yum, K., et al. Nanoscale 2, 363-372 (2010); Yum, K., et al. Biochim. Biophys. Acta, Gen. Subj. 1810, 330-338 (2011)). Compared with the conical micropipette (~1 μm in diameter), the cylindrical nanoneedle with nanoscale diameter (<~100 nm) can reach and manipulate the target area inside living cells with minimal damage to the cell membrane and with a thousand times less displacement of the intracellular materials during the cell membrane penetration process. (Chen, X., et al. Proc. Natl. Acad. Sci. U.S.A. 104, 8218-8222 (2007); Singhal, R. et al. Nat. Nanotechnol. 6, 57-64 (2011); Yum, K., et al. Nanoscale 2, 363-372 (2010); Almquist, B. D. & Melosh, N. A. Proc. Natl. Acad. Sci. U.S.A. 107, 5815-5820 (2010)). In addition, the use of nanoneedles may also allow the access to non-adherent cells due to the minimized adhesion between the nanoneedle and the cells. For example, nanoneedle-based delivery of quantum dots into the cytoplasm and nucleus of living cells, which was possible due to the use of high-aspect ratio nanoneedles with ~100 nm in diameter, has been demonstrated (Chen, X., et al. Proc. Natl. Acad. Sci. U.S.A. 104, 8218-8222 (2007); Yum, K., et al. Nano Lett. 9, 2193-2198 (2009); Yum, K., et al. Small 6, 2109-2113 (2010)).

Herein is described another simple intracellular delivery method, named nano-mechanoporation, which uses a nanoneedle to barely poke through a cell membrane and then mechanically slice the membrane to create a transient, localized nanoscale slit in the cell membrane that allows the diffusive introduction of exogenous molecules into cells (FIG. 1). The nano-mechanoporation approach can potentially have the following advantages for the single cell type intracellular delivery. First, the slender nanoneedle can gently penetrate through the thin cell membrane without inducing severe mechanical deformation and physical damage to the cell membrane and the near membrane cytoskeletal structures; second, the use of a nanoneedle in slicing through the cell membrane minimizes the drag force and thus the perturbation to the cell; third, the gap width of the slit in the membrane is defined by the diameter of the nanoneedle and is in nanoscale dimension, which facilitates the energy efficient self-sealing of the opening (effective for small disruptions of <0.2 μm) (McNeil, P. L. & Steinhardt, R. A., *Annu. Rev. Cell Dev. Biol.* 19, 697-731 (2003); McNeil, P. L. & Kirchhausen, T., *Nat. Rev. Mol. Cell Biol.* 6, 499-505 (2005)); fourth, the length of the slit is expected to be dependent on the amplitude and frequency of the slicing motion and the self-sealing rate of the membrane, and is thus externally controllable from essentially zero up to several 100 nanometers or more, which provides the possibility of a delivery method with semi-quantitative control over the amount of delivery in the extreme small quantity range; and last but not the least, the method involves only direct mechanical motion to produce the reversible nanoscale opening in the cell membrane and is comparatively straightforward and less complicated from the practical application point of view when compared to other single cell delivery methods. In the following, a general model describing the basic mechanism of the nano-mechanoporation for controlled intracellular delivery is provided, and its use for the delivery of biomolecules and species in sizes up to the size of quantum dots of ~20 nm in diameter is demonstrated.

Figure 5:
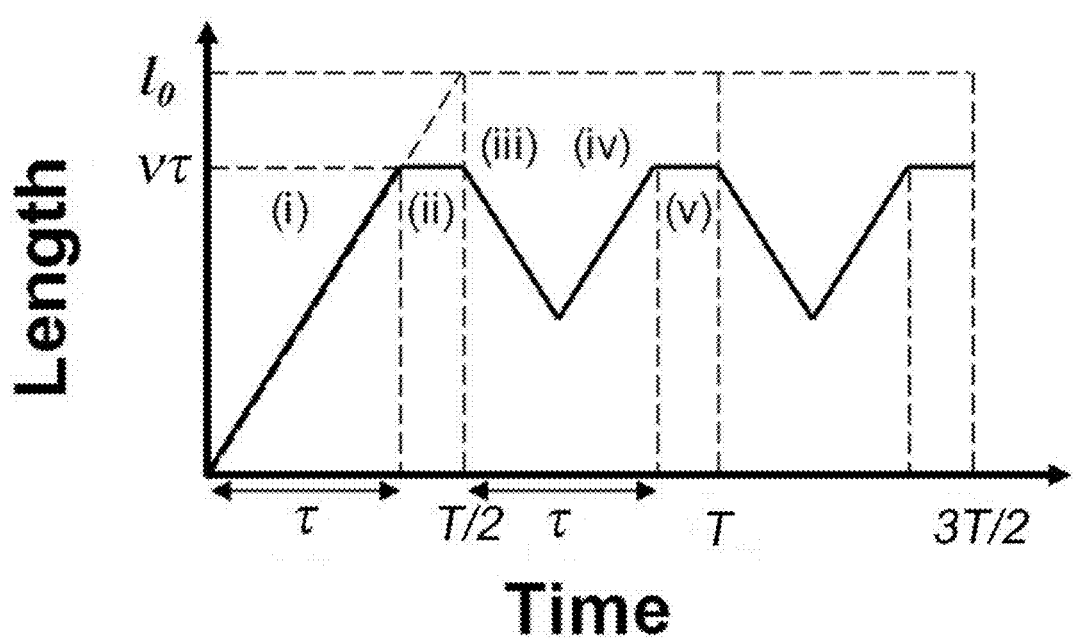

The length of the nanoscale slit, l, during the cyclic movement of the nanoneedle is related to the molecular recombination constant, k, which represents how fast the cell reseals the opening, and the frequency of the lateral motion of the nanoneedle, f. k is determined by the cell membrane repair mechanisms according to the thermodynamically-favored self-sealing process and the $Ca^{2+}$-triggered exocytosis (McNeil, P. L. & Steinhardt, R. A., *Annu. Rev. Cell Dev. Biol.* 19, 697-731 (2003); McNeil, P. L. & Kirchhausen, T., *Nat. Rev. Mol. Cell Biol.* 6, 499-505 (2005); Steinhardt, R. A., et al., *Science* 263, 390-393 (1994); Reddy, A., et al., *Cell* 106, 157-169 (2001)). A recovery time, τ, is defined that an "unzipped" membrane segment must wait to reseal upon being "unzipped" by the nanoneedle (τ is typically in the range of 10 to 120 s (McNeil, P. L. & Steinhardt, R. A., *Annu. Rev. Cell Dev. Biol.* 19, 697-731 (2003); Steinhardt, R. A., et al., *Science* 263, 390-393 (1994); Reddy, A., et al., *Cell* 106, 157-169 (2001)). τ is related to the molecular recombination constant, τ=1/k. It is assumed that k is related only to the gap of the slit-like opening, meaning the diameter of the nanoneedle used to slice through the membrane. The nanoneedle moves at a constant speed v. The cyclic period of the nanoneedle movement is designated as T and the frequency, f, is then 1/T. When τ is smaller than T/2 (or f<k/2), the average length of the slit, $l_{ave}$, created in the cell membrane can be described as a function of time as shown in FIG. 5, during one cycle of the lateral movement of the nanoneedle falls into two regimes: (i) as the nanoneedle slices through the membrane starting from left to right, the "unzipped" length of the slit linearly increases until the segment at the left end of the "unzipped" slit in the membrane begins to recover at time t=τ (the beginning time of the slicing is set to be t=0); (ii) the length of the slit remains constant as the slit segments continuously reseal starting from the left of the slit while the nanoneedle continues to slice through the membrane; (iii) when the nanoneedle reaches $l_0$ (the actual displacement of the nanoneedle at time T/2) and moves back, the length of slit begins to decrease as the nanoneedle moves back through the previously "unzipped" slit portion while the slit continues to reseal from the left. This continues until the nanoneedle meets the resealed membrane at time t=T/2+τ/2; (iv) the length of the slit increases again until the cell begins to reseal the membrane from the right end of the slit; (v) The length of the slit remains constant from time t=T/2+τ until the nanoneedle reaches the starting point on the cell membrane. As the nanoneedle moves back and forth, this cycle repeats as shown in FIG. 5. The average length of the slit, $l_{ave}$, during one repeatable cycle of the lateral movement of the nanoneedle (e.g., a cycle from time T/2 to 3T/2 in FIG. 5) is $$l_{ave} = \frac{1}{T}\int l dt,$$

where l is the actual length of the slit at time t shown in FIG. 5a. Therefore, from FIG. 5 (i.e., from the area between time T/2 to 3T/2), the average length of the opening $l_{ave}$ during one repeatable cycle of the lateral movement of the nanoneedle can be determined:

$$l_{ave} = \frac{1}{T}\left(v\tau \times T - \frac{v\tau}{2}\tau\right) = l_0[1 - (1 - f/k)^2],$$

where $l_0$=vT/2. The same result is obtained when k/2<f<k (or T/2<τ<T). On the other hand, when f>k, $l_{ave}$=$l_0$, because the segment in the slit does not have enough time to reseal during the cyclic movement of the nanoneedle.

The intracellular delivery is then facilitated by the diffusion of the target molecules dispersed in the medium into the target cell through the nanoscale slit produced in the cell membrane. The simple diffusion through the nanoscale opening is described by:

$$\frac{dC}{dt} = p\frac{DA}{wV}(C_o - C),$$

where C is the concentration of the molecule inside the cell, t is time, p is the constant that measures how effectively the molecule can enter the cell, which depends on the cell type, the cellular structure near the opening site, the size and type of the molecule, and other factors that affect the entry of the molecule into the cell, D is the diffusion coefficient of the molecule, A is the area of the opening produced by the nanoneedle, w is the thickness of the cell membrane, V is the volume of the cell, and $C_o$ is the concentration of the molecule in the medium. Thus, the concentration of the molecule delivered into the cell is a function of time t: $C=C_0(1-e^{-t/\tau})$, where the time constant τ is (wV)/(pDA). This indicates that for a target cell and the target molecules to be delivered into the cell, the amount of the molecules delivered into the cell can be controlled by controlling the area of the opening A and the duration of the movement of the nanoneedle t. The area of the opening A is simply l×d, where l is the length of the opening described previously and d is the diameter of the nanoneedle.

Figure 6A:
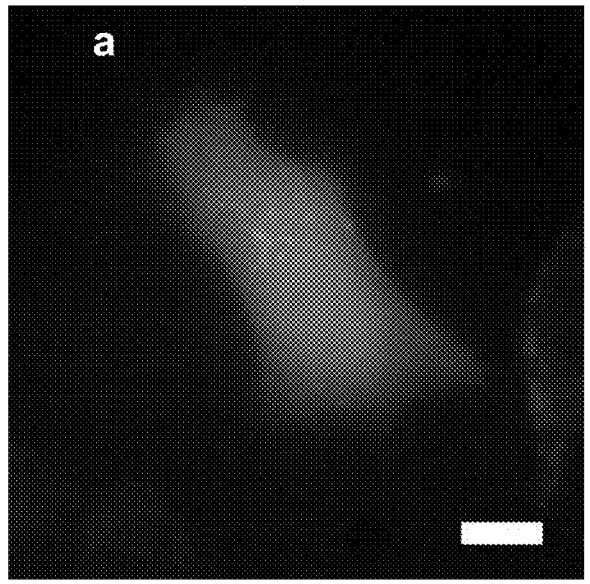
FIG. 6. Control of the amount of the Alexa Fluor 488-labeled dextrans delivered into living HeLa cells by changing the number of the cyclic movements of the nanoneedle (or the duration of the permeabilized state of the target cells), showing the increase of the fluorescence intensity with the increase of the number of the cyclic motion. The nanoneedle made 10 (a), 20 (b), and 25 (c) cyclic motions with the displacement of ~5 μm at the speed of ~1 μm/s to create the nanoscale slit in the cell membrane of the target cells. Cells with a similar size were targeted to better compare the amount of the delivered dextrans from the fluorescence of the cells. The fluorescence images are shown as acquired. Scale bar, 10 μm FIG. 7. Optical microscope image of the nanoneedle and the target cell (shown in FIG. 3) during the nano-mechanoporation process for delivering Alexa Fluor 488-labeled dextrans into the cell. The arrow shows the direction of the nanoneedle movement to create a transient nanoscale opening. Scale bar, 10 μm.
Figure 6B:
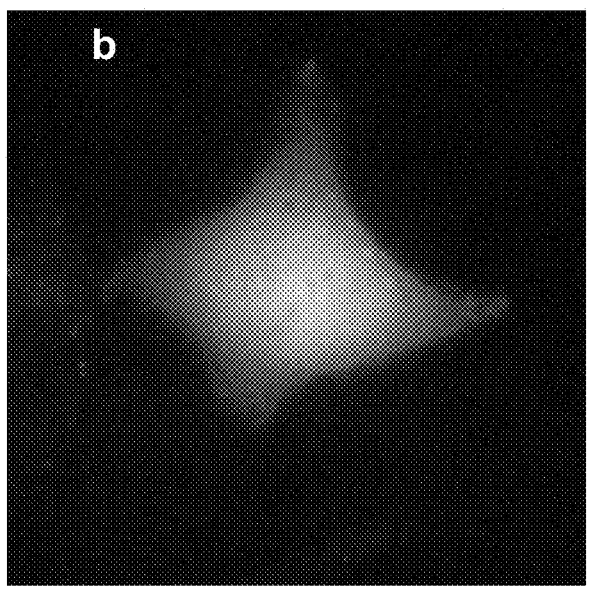
Figure 6C:
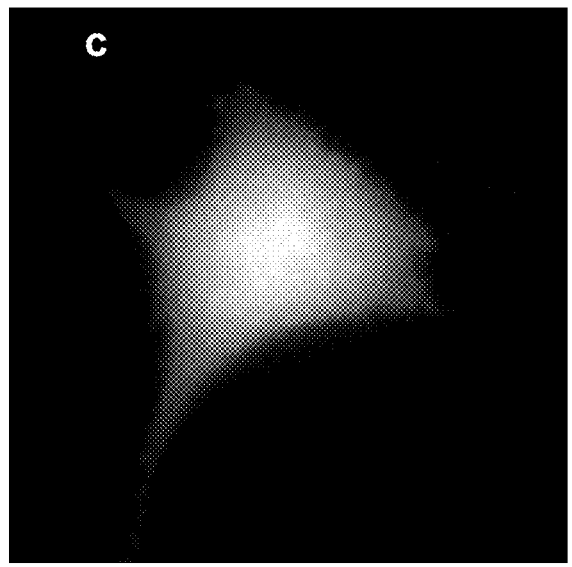

This simple model shows that the amount of the target molecules delivered into cells can essentially be controlled by changing the frequency, the displacement, and the duration of the nanoneedle movement. But, the amount of the molecules delivered into the cell also depends on cell-specific factors, such as the cell type or the ability of the cell to recover the transient opening in the cell membrane, which is associated with the duration of the permeabilized state of the cell. For instance, the amount of the molecules delivered into cells, evaluated by the fluorescence intensity of the target cells, can be influenced by changing the number (or the duration) of the cyclic movement of the nanoneedle for the cells with a similar volume (FIG. 6). However, since the delivery efficiency (or the fluorescence intensity of the molecules delivered into cells) can depend also on cell-specific factors, such as the ability of the cells to reseal the opening, the intracellular structure of the cells (especially, near the opening site), and the size, shape, and volume of target cells, control of the amount of the molecules delivered into the different kinds of cells may involve calibration for each type of cell.

To perform the nano-mechanoporation for intracellular delivery, a film-coated nanoneedle made from a chemically synthesized boron nitride nanotube was used as described previously ( ). The nanotube-based nanoneedle has a high-aspect ratio, mechanically rigid nanoscale structure with a uniform diameter (~50 to 100 nm in diameter) along its length, ideal for creating a nanoscale slit with minimal damages to cells. Alternatively, a pulled glass rod with a nanoscale tip (less than several hundred nanometers) and a gradually tapered shape was used. The glass nanoneedle was fabricated by pulling a solid glass rod (1 mm in diameter) with a micropipette puller (P-87 Pipette Puller, Sutter Instrument). The nanoneedle can also be fabricated by other types of one-dimensional nanomaterials, such as nanowires. The nanotube-based nanoneedles or glass nanoneedles were coated with a thin layer of Au/Pd (10-30 nm in thickness) to increase the mechanical integrity of the nanoneedle structure (other appropriate materials can also be selected for film coating). In the case of a glass nanoneedle, the coating is used to increase the reflectivity of the nanoneedle for visual monitoring under an optical microscope. The glass nanoneedle used in this study is different from the micropipette used for microinjection: the glass nanoneedle is a solid structure and thus has a smaller structural diameter with a gradual taper than the hollow micropipettes used for microinjection (~1 µm in diameter).

Figure 7:
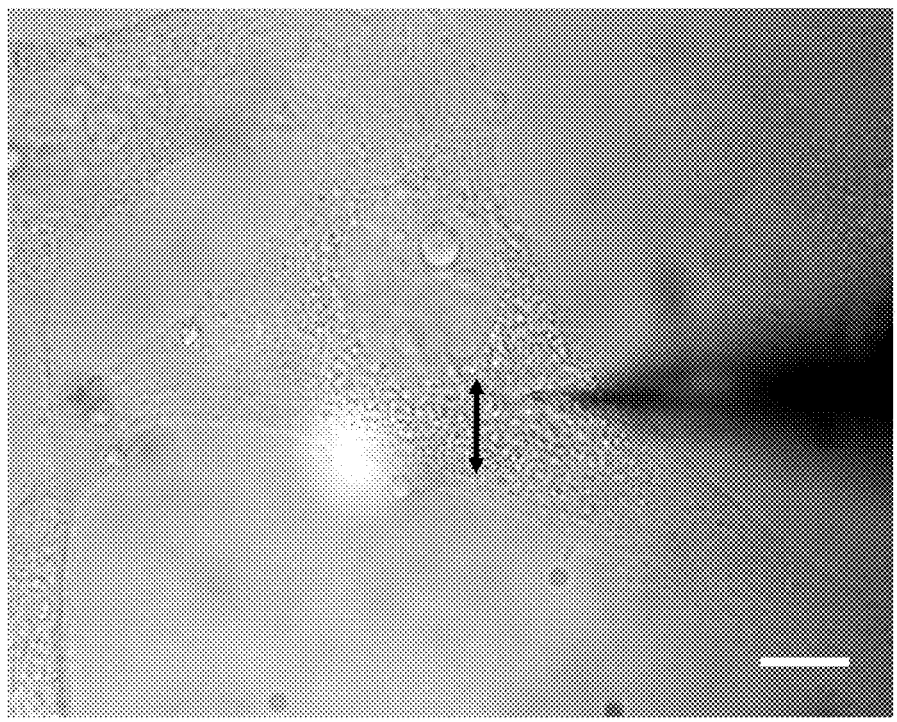

The nano-mechanoporation method was demonstrated by delivering Alexa Fluor 488-labeled dextran (3,000 MW, Invitrogen) into living HeLa cells. The fluorescent dextrans were first dispersed in the cell medium (25 µg/ml). The nanoneedle was manipulated to approach and penetrate the cell membrane along a direction of ~45° to the surface plane to the depth of ~1 to 2 µm into the cytoplasm by using a piezoelectric micromanipulator (InjectMan NI 2, Eppendorf) integrated onto an inverted microscope (Riveline, D. & Nurse, P., Nat. Methods 6, 513-514 (2009)). A nanoscale slit was then created by slicing back and forth the nanoneedle laterally through the cell membrane (perpendicular to the nanoneedle axis) with a displacement of ~1 to 5 µm for 10 to 20 times (FIG. 7). The nanoneedle was moved at a speed of ~1 µm/s; thus, this process took about ~10 to 100 s, depending on the speed and the duration of the nanoneedle movement. The nanoneedle was then retracted from the target cell. After 5 to 10 minutes, the cells were thoroughly washed with phosphate buffered saline (PBS) three times to remove excess dextrans in the medium. When a glass nanoneedle was used, the glass nanoneedle was manipulated in a way that only the tip part of the glass nanoneedle with a nanoscale diameter was inserted into the cytoplasm to minimize the cell damage.

Figure 3A:
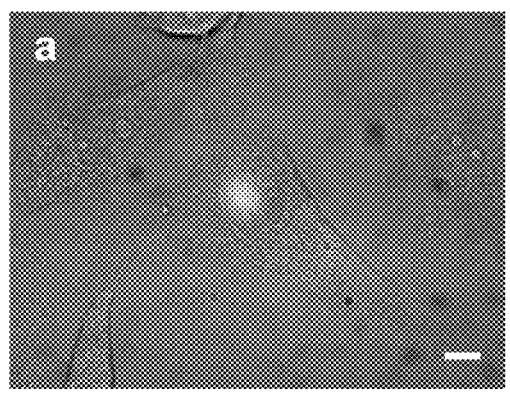
FIG. 3. Nano-mechanoporation delivery of Alexa Fluor 488-labeled dextrans into a living HeLa cell. Bright-field (a) and fluorescence (b) images after the dextran delivery, and the overlay image (c) of (a) and (b). The target cell is the same cell shown in FIG. 7. Scale bar, 10 μm.
Figure 3B:
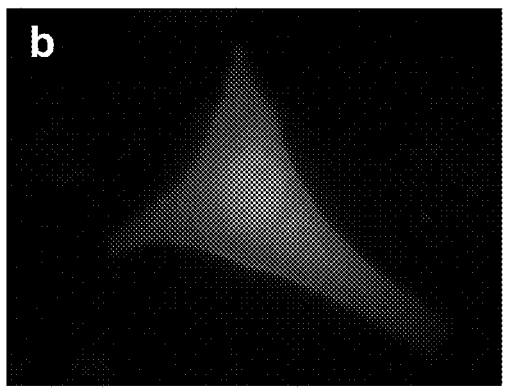
Figure 3C:
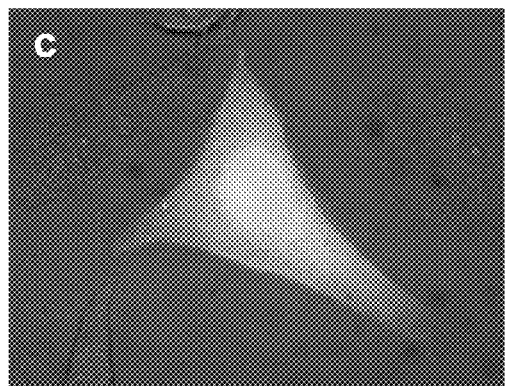

FIG. 3 shows the target cell and neighboring cells after the nano-mechanoporation process. We observed that only the cell with the nanoscale opening produced by nano-mechanoporation took up the dextran, showing fluorescence. The neighboring cells did not show fluorescence, indicating that the transient nanoscale opening created by the nanoneedle permeabilized the target cell and that the cells do not effectively uptake the dextran without the permeabilization process. When we only penetrate the cell membrane using the nanoneedle along its axial direction and retracted the nanoneedle from the cell without laterally moving the nanoneedle, we did not observe the uptake of the dextrans, suggesting that the lateral motion is required to effectively deliver molecules into the target cell. Previous studies have also showed the undetectable loss of molecules inside cells by a penetration process alone using a nanoneedle (<~100 nm in diameter) (Chen, X., et al. Proc. Natl. Acad. Sci. U.S.A. 104, 8218-8222 (2007), Yum, K., et al. Nano Lett. 9, 2193-2198 (2009)).

Figure 4A:
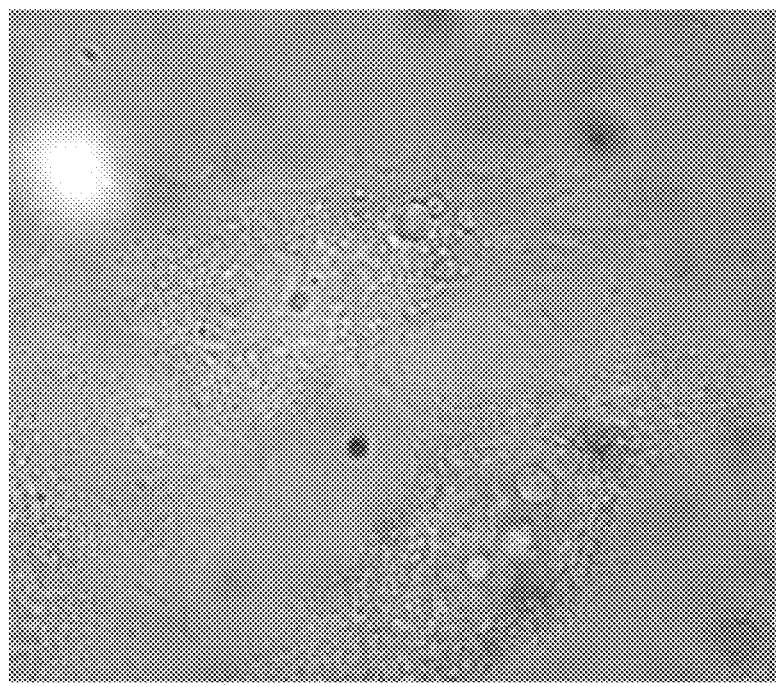
FIG. 4. Nano-mechanoporation delivery of Alexa 488-labeled phalloidin targeting actin cytoskeleton structures of a living HeLa cell (a, b) and fluorescent QDs into a living HeLa cell (c, d): bright-field (a) and fluorescence (b) images of the cell with the fluorescent phalloidin, and fluorescence image (c) and overlay of the bright field and fluorescence images (d) of the cell with QDs. Scale bar, 10 μm FIG. 5. Illustration of a relationship between the length of the membrane slit and time.
Figure 4B:
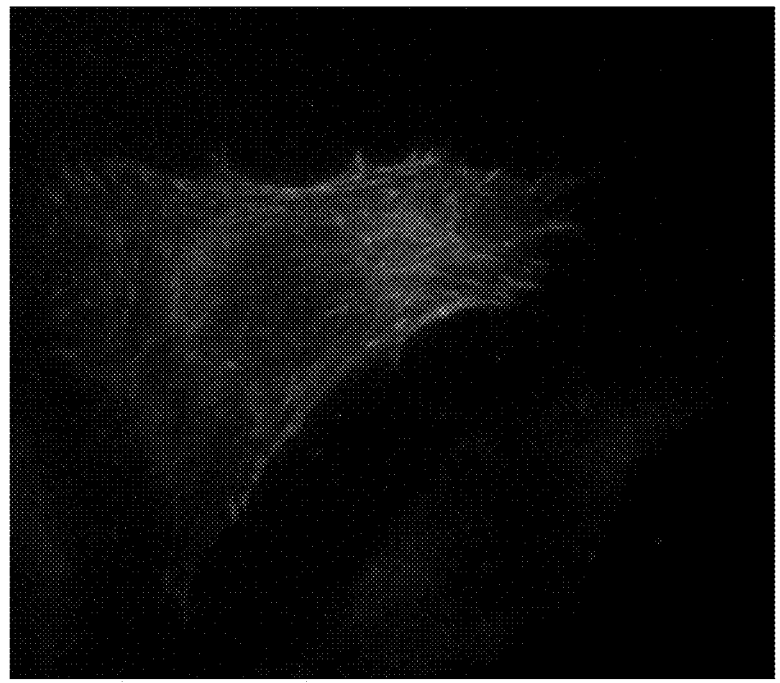

In another example, the nano-mechanoporation method was applied for delivering Alexa Fluor 488-labeled phalloidin (1,320 MW, Invitrogen) and targeting the actin cytoskeleton structure of living HeLa cells. Fluorescent phalloidin has been widely used to study actin cytoskeleton structures; the phalloidin binds to actin at the interface of F-action subunits (7). After the nano-mechanoporation process was performed on the target cell in the medium with the fluorescent phalloidin (20 U/ml), the actin structures of the target cell was visualized, confirming the targeted delivery of the fluorescent phalloidin into the cell (FIGS. 4a and 4b).

Figure 4C:
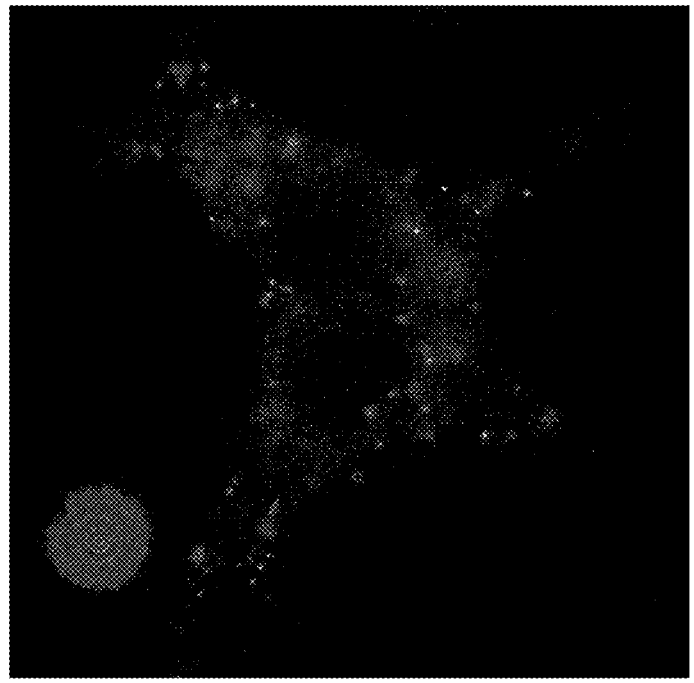
Figure 4D:
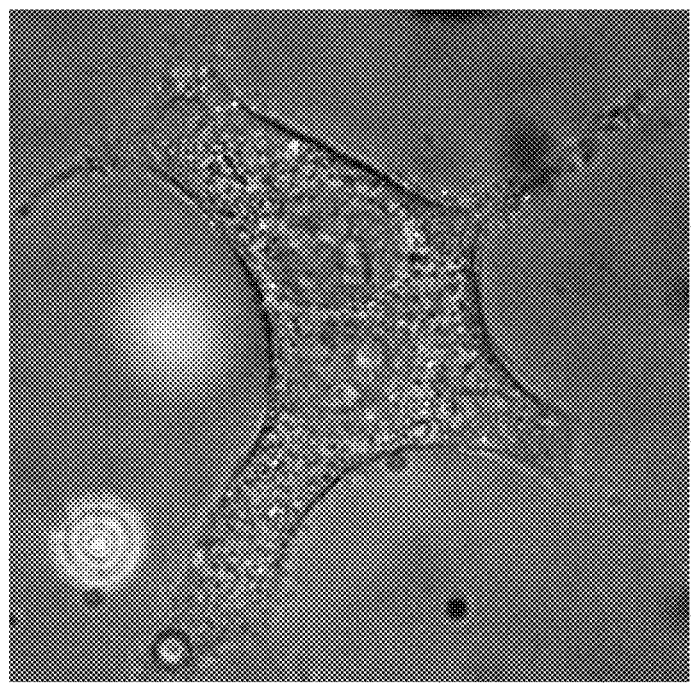
Figure 8A:
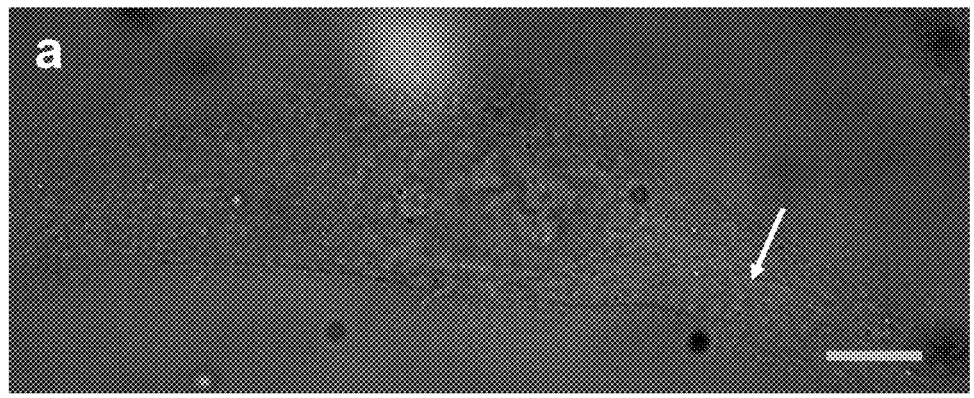
FIG. 8. Local delivery of quantum dots (QDs) into a living HeLa cell: most QDs delivered by the nano-mechanoporation were trapped to the cytoplasmic structures near the created slit. (a) Bright-field image of the target HeLa cell: the arrow indicates the site where the nanoscale slit was created by the nanoneedle. (b) Fluorescence image of QDs: most QDs are trapped near the delivery site. (c) Overlay image of (a) and (b). The arrows in (b) and (c) indicate some QDs that diffused from the opening site into the cytoplasm. Scale bar, 10 μm.
Figure 8B:
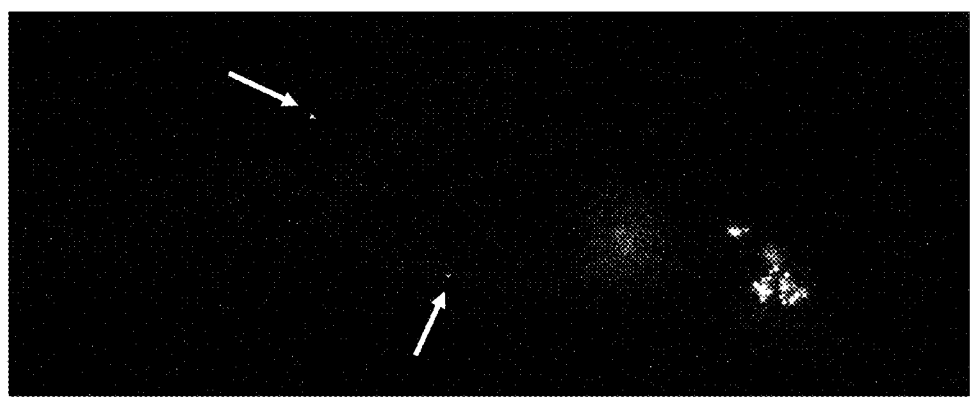
Figure 8C:
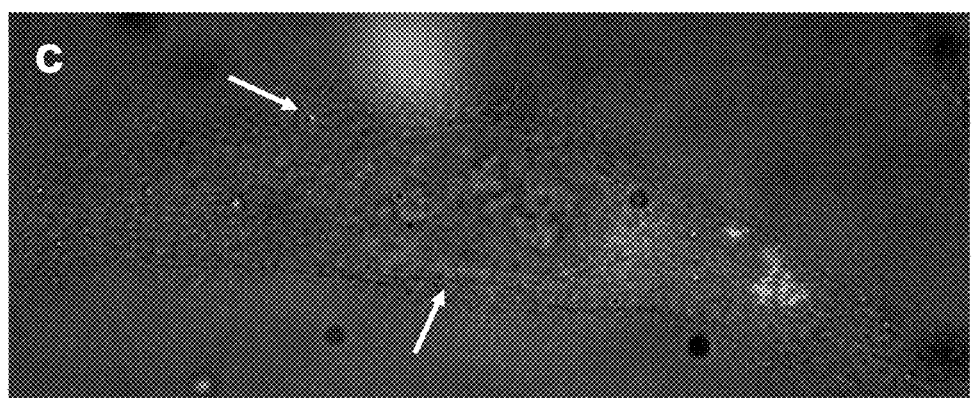

To demonstrate the delivery of larger molecules or species, delivery fluorescent quantum dots (QDs) (1 or 2 nM in the medium) with a diameter of ~20 nm (Qdot 655 streptavidin conjugates, Invitrogen) into living HeLa cells was attempted. In particular, despite the promising applications of QDs for molecular imaging inside cells due to their bright and stable fluorescence, it is still challenging to deliver well-dispersed single QDs into the cytoplasm (escaping the endocytic pathways) (Yum, K., et al. Nano Lett. 9, 2193-2198 (2009)) After the delivery process, the QDs were observed to be dispersed throughout the target cell, showing that the nano-mechanoporation process can also deliver large molecules up to 20 nm in diameter (FIGS. 4c and 4d). HeLa cells themselves do not effectively uptake streptavidin-coated QDs. For some HeLa cells, some delivered QDs concentrated near the opening site were observed (FIG. 8). This concentrated delivery of QDs near the opening site was attributed to the trapping of the delivered QDs to the intracellular structures. The pore size of the cytoplasmic meshwork (~30 to 100 nm) (Riveline, D. & Nurse, P., Nat. Methods 6, 513-514 (2009)) is comparable to the size of QDs (~20 nm); thus, the delivered QDs can be locally trapped to the cytoplasmic meshwork before further diffusing to the cytoplasm of the cell. This observation, in turn, suggests the localized delivery of the molecules by the nano-mechanoporation process. For the well-dispersed delivery of the dextran, phalloidin, and QDs (FIGS. 3 and 4), these molecules or species were initially introduced through the nanoscale opening and then diffused out to the cytoplasm. For instance, even the large QDs (~20 nm in diameter) can effectively diffuse through the cytoplasm; the diffusion coefficient of the QDs used in this study can be as high as 4 $\mu m^2/s$ in the cytoplasm of HeLa cells as reported previously (Yum, K., et al. Nano Lett. 9, 2193-2198 (2009)).

Figure 9A:
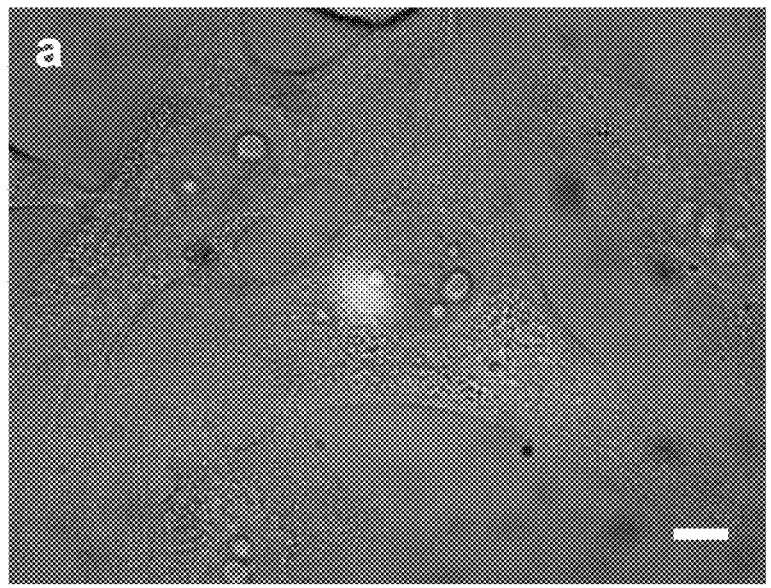
FIG. 9 Images of the target HeLa cell (shown in FIG. 3), containing Alexa Fluor 488-labeled dextrans, 12 hours after nano-mechanoporation delivery: (a) bright-field and (b) fluorescence images. The target cell was viable and did not show any distinct difference from its neighboring cells. The cells shown in the figure are the same cells shown in FIG. 3). Scale bar, 10 μm.
Figure 9B:
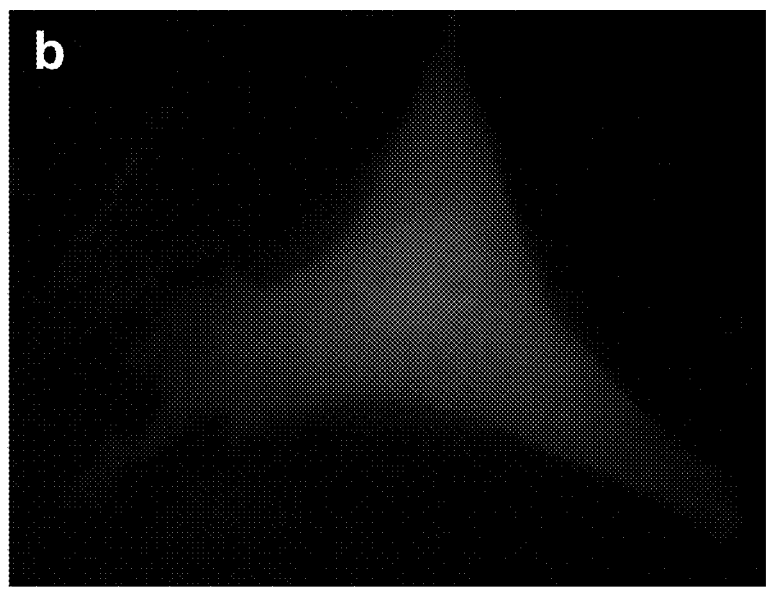

The viability of the cells after the nano-mechanoporation process was tested next. The mechanically perturbed cells were viable, as evaluated by the trypan blue assay and the cell shape (Yum, K., et al. Nano Lett. 9, 2193-2198 (2009); Yum, K., et al. Small 6, 2109-2113 (2010)). The target cells did not show any distinct difference from its neighboring cells and contained the delivered molecules for more than 12 hours (FIG. 9), showing that the cells recovered from the mechanical perturbation of the nano-mechanoporation process and the nanoscale openings in the cell membranes were indeed transitory.

In conclusion, proof of concept for the nano-mechanoporation method was demonstrated for delivering exogenous molecules into target cells, in which we used a nanoneedle to create a nanoscale slit in the cell membrane to facilitate the diffusive introduction of the molecules into cells. The intracellular delivery of both small molecules, such as fluorescent dextrans and phalloidin, and large species, such as fluorescent quantum dot nanoparticles (~20 to 25 nm in diameter), into living HeLa cells was shown. Compared with the previously reported nanoneedle-based delivery methods that require the surface functionalization of nanoneedle surface and can only deliver molecules into a limited number of cells (Chen, X., et al. Proc. Natl. Acad. Sci. U.S.A. 104, 8218-8222 (2007) Yum, K., et al. Nano Lett. 9, 2193-2198 (2009); Yum, K., et al. Small 6, 2109-2113 (2010)), the nano-mechanoporation is simple, requiring no surface functionalization, and can be used many times to deliver molecules into many cells. Thus, it would also be potentially possible to automate the nano-mechanoporation process to increase the efficiency of the intracellular delivery. Since the nano-mechanoporation process can be done by using the micromanipulator under an optical microscope, widely used in biological laboratories, this method can be readily integrated into other standard biological techniques without requiring technically demanding equipment (e.g., atomic force microscope). The method can add a new functionality to the nanoneedle for living cell studies, widening the potential applications of the nanoneedle technology for studying cellular processes and biophysical properties of living cells (Yum, K., et al. Nanoscale 2, 363-372 (2010)).

Fabrication of nanoneedles. A nanoneedle was fabricated by either attaching an individual chemically-synthesized nanotube (~50 to 100 nm in diameter) onto a microscale handle as described previously (Yum, K., et al. Nano Lett. 9, 2193-2198 (2009); Yum, K., et al. *Small* 6, 2109-2113 (2010)) or pulling a nanoscale glass rod with a micropipette puller (P-87 Pipette Puller, Sutter Instrument Co.). The nanotube-based nanoneedle has a high-aspect ratio nanoscale structure with a uniform diameter ideal for producing a nanoscale slit with minimal invasiveness. To fabricate a nanoscale glass rod, a solid glass rod (1 mm in diameter) was pulled to produce a glass rod with a nanoscale tip and gradually tapered shape to minimize the cell damage during the delivery process. After washing the nanoneedle with ethanol, the nanoneedle was coated with a thin layer of Au/Pd or Au (10-30 nm in thickness) to increase the mechanical integrity of the nanoneedle structure. The nanoscale glass nanoneedle without a metal layer is transparent and difficult to visualize under an optical microscope in the cell medium. Then, the metal-coated nanoneedle was washed with ethanol and phosphate-buffered saline (PBS) and incubated the metal-coated nanoneedle in PBS containing 1% bovine serum albumin (BSA) for 30 min to minimize nonspecific binding of intracellular proteins during the delivery process.

Cell culture and microscopy. HeLa cells were cultured in Dulbecco's modified Eagle's medium (DMEM) supplemented with 10% fetal bovine serum, 100 U/ml penicillin and 100 μg/ml streptomycin at 37° C. under 5% $CO_2$. Images were acquired with a Leica inverted epifluorescence microscope using a 63×1.32 numerical aperture oil-immersion objective and a charge-coupled device (CCD) camera (C4742-95-12ERG; Hamamatsu). Green fluorescence (dextran-Alexa 488 and phalloidin-Alexa 488) and QD images were acquired in phenol red-free media with acquisition times of 100-500 ms using a 100-W Hg lamp and a filter set (Leica 513828: BP450-490 excitation, BS510 dichroic, LP515 emission) and a QD filter set with 20 nm emission for QD 655 (Chroma), respectively. Fluorescence images were background-collected unless otherwise noted.

REFERENCES

1 Stephens, D. J. & Pepperkok, R. The many ways to cross the plasma membrane. *Proc. Natl. Acad. Sci. U.S.A.* 98, 4295-4298 (2001).
2 Luo, D. & Saltzman, W. M. Synthetic DNA delivery systems. *Nat. Biotechnol.* 18, 33-37 (2000).
3 Ruan, G., Agrawal, A., Marcus, A. I. & Nie, S. Imaging and tracking of tat peptide-conjugated quantum dots in living cells: New insights into nanoparticle uptake, intracellular transport, and vesicle shedding. *J. Am. Chem. Soc.* 129, 14759-14766 (2007).
4 Derfus, A. M., Chan, W. C. W. & Bhatia, S. N. Intracellular delivery of quantum dots for live cell labeling and organelle tracking. *Adv. Mater.* 16, 961-966 (2004).
5 Knoblauch, M., Hibberd, J. M., Gray, J. C. & van Bel, A. J. E. A galinstan expansion femtosyringe for microinjection of eukaryotic organelles and prokaryotes. *Nat. Biotechnol.* 17, 906-909 (1999).
6 Tirlapur, U. K. & Konig, K. Targeted transfection by femtosecond laser. *Nature* 418, 290-291 (2002).
7 Riveline, D. & Nurse, P. 'Injecting' yeast. *Nat. Methods* 6, 513-514 (2009).
8 Chakravarty, P., Qian, W., El-Sayed, M. A. & Prausnitz, M. R. Delivery of molecules into cells using carbon nanoparticles activated by femtosecond laser pulses. *Nat. Nanotechnol.* 5, 607-611 (2010).
9 Mehier-Humbert, S. & Guy, R. H. Physical methods for gene transfer: Improving the kinetics of gene delivery into cells. *Adv. Drug Delivery Rev.* 57, 733-753 (2005).
10 Haas, K., Sin, W.-C., Javaherian, A., Li, Z. & Cline, H. T. Single-cell electroporation for gene transfer in vivo. *Neuron* 29, 583-591 (2001).
11 Kitamura, K., Judkewitz, B., Kano, M., Denk, W. & Hausser, M. Targeted patch-clamp recordings and single-cell electroporation of unlabeled neurons in vivo. *Nat. Methods* 5, 61-67 (2008).
12 Judkewitz, B., Rizzi, M., Kitamura, K. & Hausser, M. Targeted single-cell electroporation of mammalian neurons in vivo. *Nat. Protocols* 4, 862-869 (2009).
13 Han, S. W., Nakamura, C., Obataya, I., Nakamura, N. & Miyake, J. A molecular delivery system by using afm and nanoneedle. *Biosens. Bioelectron.* 20, 2120-2125 (2005).
14 Hara, C. et al. A practical device for pinpoint delivery of molecules into multiple neurons in culture. *Brain Cell Biol.* 35, 229-237 (2006).
15 Kihara, T. et al. Development of a method to evaluate caspase-3 activity in a single cell using a nanoneedle and a fluorescent probe. *Biosens. Bioelectron.* 25, 22-27 (2009).
16 Chen, X., Kis, A., Zettl, A. & Bertozzi, C. R. A cell nanoinjector based on carbon nanotubes. *Proc. Natl. Acad. Sci. U.S.A.* 104, 8218-8222 (2007).
17 Yum, K., Na, S., Xiang, Y., Wang, N. & Yu, M.-F. Mechanochemical delivery and dynamic tracking of fluorescent quantum dots in the cytoplasm and nucleus of living cells. *Nano Lett.* 9, 2193-2198 (2009).
18 Yum, K., Wang, N. & Yu, M.-F. Electrochemically controlled deconjugation and delivery of single quantum dots into the nucleus of living cells. *Small* 6, 2109-2113 (2010).
19 Singhal, R. et al. Multifunctional carbon-nanotube cellular endoscopes. *Nat. Nanotechnol.* 6, 57-64 (2011).
20 Yum, K., Wang, N. & Yu, M.-F. Nanoneedle: A multifunctional tool for biological studies in living cells. *Nanoscale* 2, 363-372 (2010).
21 Yum, K., Yu, M.-F., Wang, N. & Xiang, Y. K. Biofunctionalized nanoneedles for the direct and site-selective delivery of probes into living cells. *Biochim. Biophys. Acta, Gen. Subj.* 1810, 330-338 (2011).
22 Almquist, B. D. & Melosh, N. A. Fusion of biomimetic stealth probes into lipid bilayer cores. *Proc. Natl. Acad. Sci. U.S.A.* 107, 5815-5820 (2010).
23 McNeil, P. L. & Steinhardt, R. A. Plasma membrane disruption: Repair, prevention, adaptation. *Annu. Rev. Cell Dev. Biol.* 19, 697-731 (2003).
24 McNeil, P. L. & Kirchhausen, T. An emergency response team for membrane repair. *Nat. Rev. Mol. Cell Biol.* 6, 499-505 (2005).
25 Steinhardt, R. A., Bi, G. & Alderton, J. M. Cell membrane resealing by a vesicular mechanism similar to neurotransmitter release. *Science* 263, 390-393 (1994).

26 Reddy, A., Caler, E. V. & Andrews, N. W. Plasma membrane repair is mediated by $ca^{2+}$-regulated exocytosis of lysosomes. *Cell* 106, 157-169 (2001).

27 Luby-Phelps, K. Cytoarchitecture and physical properties of cytoplasm: Volume, viscosity, diffusion, intracellular surface area. *Int. Rev. Cytol.* 192, 189-221 (2000).

We claim:

1. A method for creating a transient nano scale opening in the membrane of a cell, the method comprising the steps of:
   a. providing a probe and a cell, the probe having a longitudinal axis and a solid tip end, the diameter of the tip end being from 10 to 300 nm and the cell being immersed in an extracellular solution;
   b. contacting the end of the tip with the outer surface of the cell membrane;
   c. following step b), piercing through the membrane of the cell by moving the probe in a longitudinal direction until the end of the tip is located within the intracellular environment of the cell;
   d. following step c), creating an opening in the membrane of the cell by inducing motion of the tip in at least two directions transverse to the longitudinal axis of the probe, the motion of the tip comprising
      i) motion of the tip in a first direction transverse to the longitudinal axis of the probe for a first lateral displacement distance at a first average lateral speed; and
      ii) motion of the tip in a second direction transverse to the longitudinal axis of the probe for a second lateral displacement distance at a second average lateral speed, the second direction being other than the first direction;
   e. following step d), retracting the tip completely from the cell and allowing the cell membrane to reseal the created opening,
   wherein the cell is substantially stationary during steps b) through e) and the longitudinal speed of the probe in step c) and the first and second average lateral speeds of the probe in step d) are greater than zero and less than 100 microns/sec.

2. The method of claim 1, wherein the probe is connected to a positioning component and motion of the tip is induced by translating the positioning component.

3. The method of claim 2 wherein in step d)i) the positioning component is translated a first positioning component lateral translation distance and in step d)ii) the positioning component is translated a second positioning component lateral translation distance and the first and second positioning component lateral translation distances are each from 100 nm to 5 micrometers.

4. The method of claim 1 wherein the longitudinal displacement of the tip during step d) is less than 5% of the first lateral displacement distance and less than 5% of the second lateral displacement distance.

5. The method of claim 1 wherein the first and second directions are 180° apart, the first and second lateral displacement distances are the same and steps d) and e) are repeated at least 4 times.

6. The method of claim 1 wherein the total time of tip motion in step d) is from 10 seconds to 3 minutes.

7. The method of claim 1 wherein the tip has a tapered end.

8. The method of claim 1, wherein the probe comprises a nanorod or a multiwalled nanotube.

9. The method of claim 8, wherein the nanotube or nanorod material is selected from a group of materials having Young's modulus values higher than 50 GPa.

10. The method of claim 1, wherein the cell remains viable.

11. The method of claim 1, wherein the cell lacks a cell wall.

12. A method for transporting a desired chemical species or biological species through a transient nanoscale opening in the membrane of a cell, the method comprising the steps of:
   a. providing a probe and a cell, the probe having a longitudinal axis and a tip end, the diameter of the tip end being from 50 to 300 nm, the cell being immersed in an extracellular solution and the desired chemical species or biological species being provided either in the extracellular solution or within the cell;
   b. contacting the end of the tip with the outer surface of the cell membrane;
   c. following step b), piercing through the membrane of the cell by moving the probe in a longitudinal direction until the end of the tip is located within the intracellular environment of the cell;
   d. following step c), creating a permeable opening in the membrane of the cell by inducing motion of the tip in at least two directions transverse to the longitudinal axis of the probe, the motion of the tip comprising
      i) motion of the tip in a first direction transverse to the longitudinal axis of the probe for a first lateral displacement distance at a first average displacement speed; and
      ii) motion of the tip in a second direction transverse to the longitudinal axis of the probe for a second lateral displacement distance at a second lateral average displacement speed, the second direction being other than the first direction;
   e. transporting the desired chemical species or biological species through the permeable opening;
   f. following step e), retracting the tip from the cell and allowing the cell membrane to reseal the created opening;
   wherein the cell is substantially stationary during steps b) through f) and both the longitudinal speed of the probe in step c) and the first and second average lateral speeds of the probe in step d) are greater than zero and less than 100 microns/sec.

13. The method of claim 12, wherein the extracellular solution comprises exogenous molecules and the exogenous molecules diffuse into the cell in step e).

14. The method of claim 13 wherein the size of the exogenous molecules is from 1000 Dalton to 1000 kilo-Dalton.

15. The method of claim 12 wherein the extracellular solution comprises detectable tags and the detectable tags diffuse into the cell in step e).

16. The method of claim 15 wherein the detectable tags comprise nanoparticles having a size from 2 nm to 250 nm.

17. The method of claim 16 wherein the nanoparticles are quantum dots.

18. The method of claim 12 wherein endogenous molecules diffuse from the intracellular environment into the extracellular solution.

19. The method of claim 12, wherein the probe is connected to a positioning component and motion of the tip is induced by translating the positioning component.

20. The method of claim 12 wherein in step d)i) the positioning component is translated a first positioning component lateral translation distance and in step d)ii) the positioning component is translated a second positioning component lateral translation distance and the first and second positioning component lateral translation distances are each from 100 nm to 5 micrometers.

21. The method of claim 12 wherein the longitudinal displacement of the tip in step d) is less than 5% of the first lateral displacement distance and less than 5% of the second lateral displacement distance.

22. The method of claim 12 wherein the first and second directions are 180° apart, the first and second lateral displacement distances are the same and steps d) and e) are repeated at least 4 times.

23. The method of claim 12 wherein the total time of tip motion is from 10 seconds to 3 minutes.

24. The method of claim 12, wherein the tip has a tapered tip end.

25. The method of claim 12, wherein the probe comprises a nanorod or a multiwalled nanotube.

26. The method of claim 25, wherein the nanotube or nanorod material is selected from a group of materials having Young's modulus values higher than 50 GPa.

27. The method of claim 12, wherein the cell remains viable.

28. The method of claim 12, wherein the cell lacks a cell wall.

* * * * *